US009644033B2

(12) United States Patent
Cohen et al.

(10) Patent No.: US 9,644,033 B2
(45) Date of Patent: May 9, 2017

(54) PROTEIN CONSTRUCTS DESIGNED FOR TARGETING AND LYSIS OF CELLS

(71) Applicant: Universite De Reims Champagne Ardenne, Reims (FR)

(72) Inventors: Jacques Henri Max Cohen, Reims (FR); Wael Mahmoud, Reims (FR); Marcelle Tonye Libyh, Reims (FR); Nathalie Godin, Reims (FR); Annelise Gimenez, Chalons en Champangne (FR); Thierry Tabary, Reims (FR); Beatrice Donvito, Reims (FR); Daniel Baty, Marseilles (FR); Xavier Dervillez, Wincheringen (DE)

(73) Assignee: Universite De Reims Champagne Ardenne, Reims (FR)

(*) Notice: Subject to any disclaimer, the term of this patent is extended or adjusted under 35 U.S.C. 154(b) by 112 days.

(21) Appl. No.: 14/519,613

(22) Filed: Oct. 21, 2014

(65) Prior Publication Data

US 2015/0098943 A1    Apr. 9, 2015

Related U.S. Application Data

(63) Continuation of application No. 12/094,877, filed as application No. PCT/EP2006/068801 on Nov. 23, 2006, now Pat. No. 8,900,592.

(30) Foreign Application Priority Data

Nov. 23, 2005    (EP) .................................... 05292486

(51) Int. Cl.
*A61K 47/48* (2006.01)
*C07K 16/28* (2006.01)
*C07K 16/30* (2006.01)
*C07K 14/33* (2006.01)
*A61K 39/395* (2006.01)
*A61K 39/00* (2006.01)

(52) U.S. Cl.
CPC ...... *C07K 16/2896* (2013.01); *A61K 39/3955* (2013.01); *A61K 47/4833* (2013.01); *A61K 47/48261* (2013.01); *A61K 47/48484* (2013.01); *A61K 47/48561* (2013.01); *A61K 47/48576* (2013.01); *C07K 14/33* (2013.01); *C07K 16/3007* (2013.01); *A61K 2039/505* (2013.01); *C07K 2317/22* (2013.01); *C07K 2317/34* (2013.01); *C07K 2317/569* (2013.01); *C07K 2317/622* (2013.01); *C07K 2317/73* (2013.01); *C07K 2319/00* (2013.01); *C07K 2319/01* (2013.01); *C07K 2319/40* (2013.01); *C07K 2319/55* (2013.01); *C07K 2319/735* (2013.01)

(58) Field of Classification Search
CPC .......... A61K 47/48261; A61K 47/4833; A61K 47/48561; A61K 47/48576; A61K 47/48484; A61K 2039/505; C07K 16/2896; C07K 16/30; C07K 16/3007; C07K 14/33; C07K 2317/22; C07K 2317/569; C07K 2317/622; C07K 2317/34; C07K 2319/01; C07K 2319/40; C07K 2319/55; C07K 2319/735
See application file for complete search history.

(56) References Cited

U.S. PATENT DOCUMENTS

| 4,748,018 A | * | 5/1988 | Stolle ..................... C07K 16/02 424/157.1 |
| 5,443,966 A | * | 8/1995 | Fairweather ........... C07K 14/33 435/252.33 |
| 6,680,182 B1 | | 1/2004 | Khan et al. |
| 6,936,464 B1 | | 8/2005 | Zhu et al. |
| 7,074,411 B1 | * | 7/2006 | Klatzmann ............. C07K 14/47 424/192.1 |
| 7,884,190 B2 | | 2/2011 | Cohen et al. |
| 2001/0018056 A1 | | 8/2001 | Roberts |
| 2002/0172673 A1 | | 11/2002 | Klysner et al. |
| 2003/0118593 A1 | | 6/2003 | Dan et al. |

FOREIGN PATENT DOCUMENTS

| EP | 0659438 A1 | | 6/1995 |
| WO | WO-91/11461 A1 | | 8/1991 |
| WO | WO97/04109 | * | 2/1997 |
| WO | WO-00/69907 A1 | | 11/2000 |
| WO | WO-01/45734 A1 | | 6/2001 |
| WO | WO-03/035694 A2 | | 5/2003 |
| WO | WO-2004/016283 A2 | | 2/2004 |
| WO | WO-2005/077976 A2 | | 8/2005 |
| WO | WO-2005/079423 A2 | | 9/2005 |
| WO | WO-2005/106000 A1 | | 11/2005 |

OTHER PUBLICATIONS

Eberl, et al., "An Anti-CD 19 Antibody Coupled to a Tetanus Toxin Peptide Induces Efficient FAS Ligand (FASL)-Mediated Cytotoxicity of a Transformed Human B Cell Line by Specific CD4+ T Cells," Clinical and Experimental Immunology, 114:173-178 (1998).
Francis, et al, J Neurochemistry 74: 2528-2536, 2000.
Kalland, et al., "Targeting of Superantigens," Cell Biophysics, 22: 147-164 (1993).
King, et al, Nature Med 4: 1281-1286, 1998.

(Continued)

*Primary Examiner* — Phuong Huynh
(74) *Attorney, Agent, or Firm* — Cesari & McKenna, LLP

(57) ABSTRACT

The invention relates to a protein construct, comprising (i) a targeting moiety that is capable of binding to a target cell, and (ii) an effector immunogenic moiety that is capable of triggering an existing, vaccine-induced or natural, immune response. The protein construct, that is preferably in the form of a heteromultimeric protein, is useful for redirecting an immune response that was pre-existing in a patient, toward an undesired target cell.

5 Claims, 8 Drawing Sheets

(56) References Cited

OTHER PUBLICATIONS

Lilleyetal, J Immunol Methods 171: 211-226, May 1994.
Liu, et al., "FCGammari on Human B Cells Can Mediate Enhanced Antigen Presentation," Cellular Immunology, 167(2):188-194 (1996).
Merkler, et al., FASEB J 17(15): 2275-2277, Epub Oct. 16, 2003.
Oudin, et al., "A Soluble Recombinant Multimeric Anti-Rh(D) Single-Chain Fv/CRI Molecule Restores the Immune Complex Binding Ability of CRI-Deficient Erythrocytes," Journal of Immunology, 164 (3):1505-1513 (2000).
Yu, et al., Investigative Ophthalmology & Visual Science 49(2): 522-527, Feb. 2008.
Yu, et al., "Peptide-Antibody Conjugates for Tumor Therapy: A MHC-Class-II-Restricted Tetanus Toxin Peptide Coupled to an Anti-Iglight Chain Antibody Can Induce Cytotoxic Lysis of a Human B-Cell Lymphomo by Specific CD4 T Cells," International Journal of Cancer, 56(2):244-248 (1994).
Zhu, et al., Investigational New Drugs 17: 195-212, 1999.

\* cited by examiner

PROTEIN CONSTRUCTS DESIGNED FOR TARGETING AND LYSIS OF CELLS

CROSS-REFERENCE TO RELATED APPLICATIONS

The present application is a Continuation of U.S. patent application Ser. No. 12/094,877, filed on May 23, 2008, now U.S. Pat. No. 8,900,592, which is the National Stage under 35 U.S.C. §371 of International Application No. PCT/EP2006/068801, filed on Nov. 23, 2006, which claims the benefit of European Application No. 05292486.7, filed Nov. 23, 2005. The content of these applications are hereby incorporated by reference in its entirety.

BACKGROUND OF THE INVENTION

Field of the Invention

The present invention relates to a protein construct, useful for redirecting an existing immune response, toward an undesired target cell.

Background Information

Natural immune response is not sufficient to destroy undesired cells such as tumor cells. Many efforts have been made to target these cells, in order to obtain a better immune response or a direct cytotoxicity. In this purpose, bi-functional molecules, optionally heteromultimeric bi-functional molecules, have been proposed. In this context immunotoxins have been designed, that contain targeting domains that direct the molecules to target cells of interest (e.g., effector T lymphocytes) and toxic domains that kill the target cells. U.S. Pat. No. 6,492,498 describes a fusion protein molecule containing a toxic domain, a targeting domain, and at least one heterologous coupling moiety. U.S. Pat. No. 6,492,498 further describes multimeric forms of this protein molecule.

However such approach is still not fully satisfying. Firstly, all target cells are not destroyed. Secondly, immunotoxins that do not reach the target may be toxic to other cells.

SUMMARY OF THE INVENTION

A subject of the invention is thus a protein construct, comprising (i) a targeting moiety that is capable of binding to a target cell, and (ii) an effector immunogenic moiety that is capable of triggering an existing, vaccine-induced or natural, immune response. Most preferably the immune response is antibody-induced.

The protein construct can be in monomeric form, or, advantageously in a multimeric form.

A preferred multimeric protein comprises a multimerizing scaffold bearing (i) at least one targeting moiety that is capable of binding to a target cell, and (ii) at least two, preferably between six and eight, effector immunogenic moieties that are capable of triggering an existing, vaccine-induced or natural, immune response.

In a most preferred embodiment, the scaffold comprises the C-terminal part of the alpha chain of C4BP and/or of the beta chain of C4BP, and the effector immunogenic moiety is fragment C of tetanus toxin.

The invention further provides a pharmaceutical composition comprising such protein constructs, in association with a pharmaceutically acceptable carrier.

Another subject of the invention is the use of such protein constructs, for the preparation of a medicament intended for redirecting an immune response that was pre-existing in a patient, toward an undesired target cell, e.g. a tumor cell or an erythrocyte.

Advantageously the medicament causes destruction of said target cell. Complexes are formed between the protein constructs of the invention and target cells, leading to an activation of downstream biologic effector mechanisms, such as complement or Antibody Dependant Cell Cytotoxicity (ADCC), that result in the elimination of the target.

A particular subject of the invention is the use of a heteromultimeric protein comprising fragment C of tetanus toxin as an effector moiety, for the preparation of a medicament intended for redirecting an immune response in a patient who is naturally vaccinated against tetanus, or was previously subjected to a vaccination against tetanus. The anti-tetanus antibodies are recruited by the fragment C of tetanus toxin of the protein constructs, and can activate the complement system or cytotoxic cells, ultimately leading to the lysis of the target cell.

Targeting Moiety

The targeting moiety is a polypeptide that shows affinity for a target cell. Preferably it allows a specific binding to said target cell.

In a preferred embodiment, it is selected from the group consisting of an antibody, a binding fragment thereof, a ligand to a target cell receptor, and a lectin.

As used herein, the term "binding fragments" of antibodies refers to antigen-binding fragments, e.g., Fab, $F(ab')_2$, Fv, and single chain Fv fragments.

Antibodies, or antibody fragments can be specific for (i.e., will have significant binding affinity for) a molecule expressed on the surface of a target cell of interest. Thus, they can have specific binding affinity for molecules such as T cell surface molecules (e.g., CD3 polypeptides, CD4, CD8, CD2, CD7, cytokine or growth factor receptors, or TCR), B cell surface molecules (e.g., CD19, CD20, CD22, cytokine or growth factor receptors, or Ig molecules), molecules expressed on tumor cells, and molecules expressed on the surface of infected target cells (e.g., viral proteins and glycoproteins).

More particularly, the targeting moiety may be an antibody, or a binding fragment thereof, against a tumor associated antigen, e.g. the carcinoembryonic antigen. Carcinoembryonic antigen (CEA) is a tumor marker which can be present on the membrane cells surface of various cancer such as pancreatic, gastric, colonic, ovarian and breast carcinoma. Other tumor associated antigens are, among others, oncofetal antigens, MART-1, Mage-1, Mage-3, gp 100, tyrosinase, CEA, her2/neu, PSA, CA-125, erb-2, Muc-1, Muc-2, point mutated ras oncogenes, point mutated p53 oncogenes, and TAG-72.

It may also be an antibody, or a binding fragment thereof, against a Rhesus antigen, especially Rhesus D antigen.

Antibodies against Glycophorin A are useful to target erythrocytes. Glycophorin A (GPA) is an abundant glycoprotein on the human erythrocyte membrane surface ($0.3\times10^6$ to $1.2\times10^6$ sites/erythrocyte). In the Examples presented herein, a recombinant anti-GPA scFv (30 kDa) was derived from a monoclonal IgG2b antibody (R18) which has a high affinity for the glycophorin A.

The targeting moiety can also be immunoglobulin (Ig) molecules of irrelevant specificity (or immunoglobulin molecule fragments that include or contain only an Fc portion) that can bind to an Fc receptor (FcR) on the surface of a target cell (e.g., a tumor cell).

The targeting moiety can further be cytokines, TNF-alpha, vascular endothelial growth factor (VEGF), and epidermal growth factor (EGF) colony stimulating factors (e.g., GM-CSF), hormones (e.g., insulin, or growth hormone), ligands for signal transduction receptors (e.g., CD40 ligand, an MHC class I molecule or fragments of an MHC molecule involved in binding to CD8, an MHC class II molecule or the fragment of an MHC class II molecule involved in binding to CD4), or ligands for adhesion receptors, e.g., ICAM-1, ICAM-2, or fibronectin or a domain (e.g., one containing one or more of the "Arg-Gly-Asp" repeats) of fibronectin involved in binding to integrin molecules. In addition a targeting domain could be Fas or Fas ligand or other death domain containing polypeptides (e.g., members of the TNF receptor family) or ligands for such polypeptides (e.g., TNF-alpha, or TWEAK).

Effector Moiety

The effector moiety refers to a polypeptide that activates an existing immune response. An existing immune response includes a natural immune response or the immune response induced by a vaccination against a pathogenic agent, e.g. a virus or a bacteria. The term "natural immune response" refers the immune response that has developed naturally in a patient. Such natural immune response includes the antibodies that have been produced by the body after an infection, or the antibodies of spontaneous existence, that recognize the cell elements, e.g. anti-actin antibodies or other natural antibodies of weak affinity and high connectivity.

Such effector moiety is not toxic by itself. It contains B cell epitope(s) and is capable of inducing an antibody response.

In a preferred embodiment, the effector moiety is a vaccine antigen, e.g. a toxin fragment that is immunogenic but non-toxic.

For example, it may be fragment C of tetanus toxin (TTFgC). Tetanus Toxin (TT) is a potent neurotoxin of molecular weight 150 KDa produced by the anaerobic bacterium *Clostridium tetani*. It consists of two polypeptide chains connected through an interchain disulfide bound. The larger fragment or heavy chain (100 KDa) contains the toxin's binding and translocation domain. The smaller polypeptide or light chain (50 KDa) is a zinc-dependant protease which cleaves synaptobrevin 2, blocking exocytosis of inhibitory transmitters. The Tetanus Toxin Fragment C (TTFgC) which is the 50 KDa C-terminal portion of the heavy chain, retains the neuronal and protein-binding activity and the uptake properties of the holotoxin without the toxic activity. TTFgC has the advantage of being non-toxic and virtually devoid of any action on the nerve processes in which they are transported. TTFgC is a known immunogen protective against tetanus, which was used for cell-lysis.

Other examples of effector moiety include an anatoxic fragment of diphtheria toxin, or a surface antigen of a virus, such as Hepatitis B virus.

In another embodiment, the effector moiety can further be a self-antigen against which natural antibodies exist. Further examples of effector moiety thus include antigenic cytoskeleton proteins, e.g. actin or tubulin, or antigenic fragments thereof. Indeed, antibodies of the IgM, IgG and IgA classes, reactive with a variety of serum proteins, cell surface structures and intracellular structures, are 'naturally' found in all normal individuals. Present in human cord blood and in 'antigen-free' mice, their variable-region repertoire is selected by antigenic structures in the body and remains conserved throughout life. Encoded by germline genes with no, or few, mutations, natural autoantibodies are characteristically 'multireactive' and do not undergo affinity maturation in normal individuals. Natural autoantibodies participate in the equilibrium of the immune system, contributing to controlled production of antibodies, accelerated elimination of external antigens or aged autoantigens, and to triggering of a specific immune response. They may participate in a variety of physiological activities, from immune regulation, homeostasis and repertoire selection, to resistance to infections, transport and functional modulation of biologically active molecules (Coutinho A, Kazatchkine M D, Avrameas S, Curr Opin Immunol. 1995 Dec. 7(6):812-8; Ternynck T, Druet P, Avrameas S.Rev Prat. 1994 Jan. 1; 44(1):36-8; Avrameas S, Ternynck T, Mol Immunol. 1993 Aug. 30(12):1133-42).

The Protein Construct

The targeting moiety and the effector moiety can be linked by a variety of methods.

In a preferred embodiment, they may be linked by means of a multimerizing scaffold, and the protein construct then preferably is in the form of a heteromultimeric protein. In a more preferred embodiment, the scaffold is a C4BP protein, or comprises a multimerizing fragment thereof [Libyh et al, Blood. 1997, 90(10):3978-83, Oudin et al, 2000, Journal of Immunology, 164,1505, and WO97/04109].

More particularly, the scaffold comprises the C-terminal part of the alpha chain of C4BP and/or of the beta chain of C4BP.

The C4BP molecule is found in normal human plasma. It has a spider-like structure made of seven α-chains and one β-chain but minor forms made from only seven α-chains or five α/1 β-chain molecules have also been described. The basic repetitive structure of both chains is termed short consensus repeat (SCR). Each SCR of about 60 amino acids includes two intrachain disulfide bridges. The C-terminal part of the C4BP lacks biological function and is responsible for the polymerization of the molecule in the cytoplasm of C4BP producing cells. The C-terminal part of the α-chain of C4BP is preferred to set up homo and hetero multimers, due to these properties as well as to its nonimmunogenicity of a normal human plasma protein.

The heteromultimeric protein construct may preferably comprise at least one targeting moiety and at least 2, preferably at least 5 or 6 effector moieties.

Such heteromultimeric protein construct can be prepared by various methods. In a particular embodiment it is prepared by a method comprising a) transfecting host cells with a nucleic acid vector that encodes the targeting moiety fused to a first scaffold polypeptide, and with a nucleic acid vector that encodes the effector moiety fused to a second scaffold polypeptide, wherein said second scaffold polypeptide is capable of multimerization with said first scaffold polypeptide, b) expressing the expression products and allowing them to multimerize;

c) recovering the heteromultimeric protein constructs thus produced.

More particularly the host cells can be co-transfected with said two nucleic acid vectors.

Alternatively the method can comprise a1) transfecting a host cell with a nucleic acid vector that encodes the targeting moiety fused to a first scaffold polypeptide, under conditions allowing expression of said targeting moiety fused to said scaffold polypeptide;

a2) transfecting another host cell with a nucleic acid vector that encodes the effector moiety fused to a second scaffold polypeptide, under conditions allowing expression of said targeting moiety fused to said scaffold polypeptide, wherein said second scaffold polypeptide is capable of multimerization with said first scaffold polypeptide, b) recovering the expression products and contacting them under conditions that allow them to multimerize.

In preferred embodiments, it is described two models of heterofunctional molecules that bind to cells and induce the complement-dependent cells lysis.

Multimerizations of TTFgC with anti-GPA scFv or anti-CEA VHH were provided by the multimerizing potential of the complement binding protein (C4BP).

cDNA containing the C-terminal part of the C4BPα coding sequence was fused with the sequence coding for the protein of interest (TTFgC, anti-GPA scFv or anti-CEA) and C4BPIβ coding sequence was fused with the anti-GPA scFv sequence coding and then transfected in eukaryotic or insect cells as a single-phase construct for in vitro protein expression. The chimera proteins spontaneously multimerize in the cytoplasm of transfected cells that secrete covalently linked multimeres. Cotransfection of cells by two different vectors containing sequences coding for two distinct multimeric molecules lead to the production of a heteromultimeric protein with valences from both molecules covalently linked together by disulfide bridges.

In a first model, a TTFgC-C4BPα/anti-GPA scFv-C4BPα heteromultimeric molecule was produced. In vitro this heteromultimeric protein was able to bind to the erythrocyte surface and to induce an erythrocyte complement-dependent lysis. A TTFgC-C4BPα/anti-GPA scFv-C4BPα heteromultimeric molecule was also produced. In vitro this heteromultimeric protein was able to bind to the erythrocyte surface. In a second model TTFgC-C4BPα/anti-CEA-C4BPα molecule was also produced. This heteromultimeric molecule allowed the redirection of existing TT vaccine induced immuno-response towards human colon carcinoma cells tumor cells by targeting and destruction of them.

In another embodiment, the protein construct is a monomer comprising a targeting moiety and an effector moiety. The targeting moiety and the effector moiety can be linked by any methods such as fusion or covalent binding. The present invention further provides nucleic acids that encode such monomer fusion proteins. Such nucleic acid may be useful for the preparation of a medicament intended for redirecting an immune response that was pre-existing in a patient, toward an undesired target cell.

The monomer fusion proteins of the invention can further be linked to each other by methods known in the art, to form multimeric proteins. For example, a terminal or internal cysteine residue on one monomer can be utilized to form a disulfide bond with a terminal or internal cysteine residue on another monomer. Monomers can also be cross-linked using any of a number of known chemical cross linkers.

While these cross-linking methods can involve residues ("coupling moieties") that are native to either of the domains of the monomers, they can also be used to cross-link non-native ("heterologous") residues incorporated into the polypeptide chains. While not necessarily the case, such residues will generally be amino acids (e.g., cysteine, lysine, arginine, or any N-terminal amino acid). The coupling moieties are preferably at the termini (C or N) of the monomers. They can be, as indicated above, a cysteine residue on each monomer, or a cysteine on one and a lysine on the other. Where they are two cysteine residues, cross-linking can be effected by, for example, exposing the monomers to oxidizing conditions.

The multimeric proteins can contain two or more (e.g., three, four, five, six, seven or eight) of the monomeric proteins described above. Each monomer can be identical, i.e., contain the same targeting and effector moieties and have the same amino acid sequence. Alternatively, they can be different. Thus, they can contain, for example, the same targeting moieties but different effector moieties, different targeting moieties but the same effector moieties, or different targeting moieties and different effector moieties. Where different targeting moieties are used, they will generally have significant binding affinity for either the same cell-surface molecule or for different molecules on the surface of the same cell.

Therapeutic Applications

The protein construct of the invention is useful to target and kill undesired cells in vivo.

It is herein described a method of killing undesired cells in a patient, wherein said patient is administered with an effective amount of the protein construct of the invention.

Destruction of Rhesus D erythrocytes is of particular interest, as it is a source of foetus-mother incompatibility.

Other appropriate patients include, without limitation, transplant (e.g., bone marrow, heart, kidney, liver, pancreas, lung) recipients, those with any of a variety of tumors (e.g., hematological cancers such as leukemias and lymphomas, neurological tumors such as astrocytomas or glioblastomas, melanoma, breast cancer, lung cancer, head and neck cancer, gastrointestinal tumors, genitourinary tumors, and ovarian tumors, bone tumors, vascular tissue tumors), those with any of a variety of autoimmune diseases, or those with an infectious disease involving an intracellular microorganism (e.g., Mycobacterium tuberculosis, Salmonella, influenza virus, measles virus, hepatitis C virus, human immunodeficiency virus, and Plasmodium falciparum). In transplant recipients, the protein construct is delivered, for example, to T cells, thereby resulting in the death of a substantial number, if not all, of the T cells. Delivery of an appropriate protein construct to tumor cells can result in the death of a substantial number, if not all, of the tumor cells. In the case of infection, the protein construct is delivered to the infected cells, thereby resulting in the death of a substantial number of, in not all, the cells and thus a substantial decrease in the number of, if not total elimination of, the microorganisms. In autoimmune diseases, the protein construct can contain a targeting moiety directed at the T cells (CD4+ and/or CD8+) and/or B cells capable of producing antibodies that are involved in the tissue destructive immune responses of the diseases.

The effector moiety is selected according to the immune profile of the patient, i.e. according to the existing immune response the patient has developed, either naturally, or further to a vaccination.

For in vivo administration, the protein constructs are generally associated with a pharmaceutically-acceptable carrier (e.g., physiological saline) and administered orally or by intravenous infusion, or injected subcutaneously, intramuscularly, intraperitoneally, intrarectally, intravaginally, intranasally, intragastrically, intratracheally, or intrapulmonarily. They are preferably delivered directly to an appropriate tissue, e.g., lymphoid tissue such as spleen, lymph nodes, or gut-associated lymphoid tissue in which an immune response (as, for example, in GVHD or an autoimmune disease) is occurring. The dosage required depends on the choice of the route of administration, the nature of the formulation, and the patient. Suitable dosages are in the range of 0.01-100.0 μg/kg.

In another in vivo approach, an expression vector containing one or more coding sequences encoding one or more fusion proteins of the invention, each coding sequence being separately transcribed, can be delivered to an appropriate cell of the subject. Alternatively, more than one expression vector, each containing a coding sequence encoding a different fusion protein, can be delivered to the appropriate cell. As the latter process would require that each expression vector be incorporated into a cell of interest, the approach using a single vector containing one or more coding sequences will be more efficient. The fusion proteins are designed such that, after translation, the fusion proteins will be multimerized by normal physiological mechanisms within the cell. Thus, for example, the fusion proteins can be linked by the formation of inter-fusion protein disulfide bonds or by non-covalent hydrophobic interactions between two or more fusion proteins.

For example, expression can be directed to a transplanted tissue or cell. An appropriate expression vector can, for example, be delivered directly to a tumor or, at the time of surgery, to tissues in the region of the body of the subject from which the tumor was surgically removed. It is not required that expression of the fusion protein be directed to the target cell itself. Indeed, expression will preferably not be by the target cell alone since, in this case, killing of the target cells by the protein construct would result in the depletion of the source of the protein construct.

The figures and examples below illustrate the invention without limiting its scope.

BRIEF DESCRIPTION OF THE DRAWINGS

FIG. 1 shows the map of the TTFgC-C4BPα construct for transfection in 293T cells.

FIG. 3 shows the map of the TTFgC-C4BPα construct for transfection in SF9 cells.

FIG. 4 shows the map of the anti-GPA scFv-C4BPα construct for transfection in SF9 cells.

FIG. 5. Direct hemagglutination of erythrocytes (E). Incubation of E with:

1. R18 antibody (positive control).
2. TTFgC-C4BPα construct transfected 293T cell supernatant
3. anti-GPA scFv-C4BPα construct transfected 293T cell supernatant
4. TTFgC-C4BPα and anti-GPA ScFv-C4BPα constructs transfected 293T cell supernatant FIG. 6. Analysis of TTFgC-C4BPα/anti-GPA scFv-C4BPα and TTFgC-C4BPα/anti-GPA scFv-C4BPβ binding on E by flow cytometry. E were incubated with:

a. TTFgC-C4BPα transfected cell supernatant.
b. anti-GPA scFv-C4BPα transfected cell supernatant.
c. Non-transfected cell supernatant.
d. TTFgC-C4BPα/anti-GPA scFv-C4BPβ transfected cell supernatant.
e. TTFgC-C4BPα/anti-GPA scFv-C4BPβ transfected cell supernatant.
f. TTFgC-C4BPα/anti-GPA scFv-C4BPα transfected cell supernatant.

FIG. 7. TTFgC-C4BPα/anti-GPA scFv-C4BPα distribution pattern was analyzed using fluorescence microscopy.

FIG. 8. Analysis of TTFgC-C4BPα/anti-CEA VHH-C4BPα binding by flow cytometry. LS174T cell were incubated with:

a. TTFgC-C4BPα transfected cell supernatant.
b. Multimeric anti-CEA VHH-C4BPα transfected cell supernatant.
c. TTFgC-C4BPα/anti-CEA VHH-C4BPα transfected cell supernatant.
d. Monomeric anti-CEA VHH-c-myc transfected cell supernatant as positive control FIG. 9. Analysis of TTFgC-C4BPα/anti-CEA VHH-C4BPα distribution pattern using fluorescence microscopy.

FIG. 10. Analysis of cascade complement activation by TTFgC-C4BPα/anti-GPA scFv-C4BPα molecules, revealed by a biotinylated monoclonal anti-human C4d antibody. Erythrocytes were incubated with:

a. TTFgC-C4BPα transfected cell supernatant and heat inactivated serum containing high level of anti-TTFgC.
b. TTFgC-C4BPα transfected cell supernatant and C5-deficient serum.
c. TTFgC-C4BPα/anti-GPA scFv-C4BPα cell supernatant and C5-deficient serum.
d. TTFgC-C4BPα transfected cell supernatant FIG. 11. Analysis of (A) C3b (revealed by fluorescein-labeled goat antiserum) and (B) C4d (revealed by anti-C4d biotinylated monoclonal anti-Human C4d antibody) distribution pattern by fluorescence microscopy.

FIG. 12. O.D (630-405 nm) corresponds to the absorbance of haemoglobin; which indicates the degree of erythrocyte lysis.

a. Erythrocytes lysed with repetitive cycles of freezing/defreezing (100% of erythrocyte lysis).
b. Erythrocytes with TTFgC-C4BPα/anti-GPA scFv-C4BPα supernatant.
c. Erythrocytes with TTFgC-C4BPα supernatant.
d. Erythrocytes with anti-GPA scFv-C4BPα supernatant.
e. Erythrocytes with non-transfected cell supernatant.
f. TTFgC-C4BPα/anti-GPA scFv-C4BPα supernatant, without erythrocytes. The minimal value of O.D (~0.200) corresponded to the absorbance of the serum.

DETAILED DESCRIPTION

Examples

Example 1

Targeting and Lysis of Cells Using Heteromultimeric Recombinant Proteins

Materials and Methods

1 Cloning of Anti-GPA Heavy and Light Chain Variable Region Coding Sequences and Assembly into an scFv The Single-chain Fv (scFv) was constructed according to the method described by Marks et al. Briefly, RNA was extracted from mouse hybridoma secreting the monoclonal anti-glycophorin antibody R18 (kindly provided by J. P CARTRON, Institut National de Transfusion Sanguine, Paris, France). cDNA was generated using the Mouse scFv Module kit (Amersham Pharmacia, Orsay, France), the $V_H$ and $V_L$ genes were amplified by PCR using primers specific for the variable region of each chain and, finally, assembled into a single gene using a linker DNA fragment which maintains the correct reading frame. The assembly reaction ultimately produced the scFv gene where the $V_H$ region was linked to the $V_L$ region through a sequence encoding a $(Gly_4Ser)_3$ peptide.

2 DNA Constructions and 293T Cell Transfections 2.1 Cloning of the TTFgC-C4BPα Construct DNA encoding TTFgC was kindly provided by P. MUNRO (Unite INSERM U 452, Facultéde Médecine de Nice, France).

PCR amplification of TTFgC DNA was achieved by forward primer: 5'-CGCGAGAGATCTCTGGATTGT-TGGGTTGATAAT-3' (SEQ ID NO:9) and reverse primer: 5'-CGCGAGTCCGGAATCATTTGTCCATCCTTCATC-3' (SEQ ID NO:10).

Figure 2:
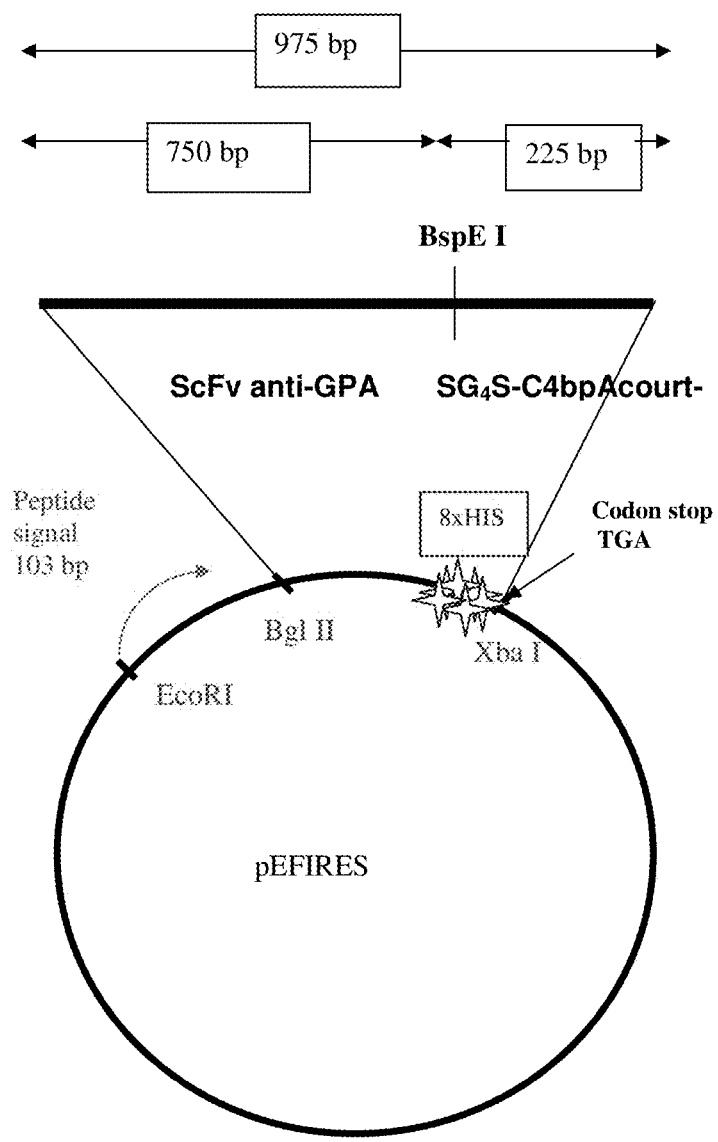
FIG. 2 shows the map of the anti-GPA scFv-C4BPα construct for transfection in 293T cells.

Restriction sites BglII and BspEI (underlined sequences) were inserted into forward and reverse primers respectively to facilitate TTFgC subcloning. A 100 µl reaction mixture was prepared, containing 500 ng of DNA, 500 ng of 3' and 5' primers, 16 nM dNTP, 10 mM Tris-HCl (pH 8.3), 50 mM KCl, 1.5 mM MgCl$_2$ and 2 U of AmpliTaq DNA polymerase (Perkin-Elmer, Roissy, France), then subjected to 30 cycles of amplification [30 s at 94° C., 30 s at 42° C., 2 min at 72° C.] using a GenAmp PCR System 9600 (Perkin-Elmer). PCR products were analyzed by electrophoresis on a 2% agarose gel.

PCR amplification of C4BPα was fulfilled by forward primer: 5'-CGCGAGTCCGGAGGCGGTGGCTCGAC-CGGA-3' (SEQ ID NO:11) (Eurogentec, Angers, France) and reverse primer: 5'-CGCGAGTCTAGATTATCAGT-GATGGTGATGGTGATGGTGGTGGATTAGTTCTT TATC-3' (SEQ ID NO:12) (Eurogentec, Angers, France). Restriction sites BspEI and XbaI (underlined sequences) were inserted into forward and reverse primers respectively to facilitate C4BPα subcloning. A 100 µl reaction mixture was prepared, containing 500 ng of DNA, 500 ng of 3' and 5' primers, 16 nM dNTP, 10 mM Tris-HCl (pH 8.3), 50 mM KCl, 1.5 mM MgCl$_2$ and 2 U of AmpliTaq DNA polymerase (Perkin-Elmer, Roissy, France), then subjected to 30 cycles of amplification [30 s at 94° C., 30 s at 60° C., 30 s at 72° C.] using a GenAmp PCR System 9600 (Perkin-Elmer).

Figure 1:
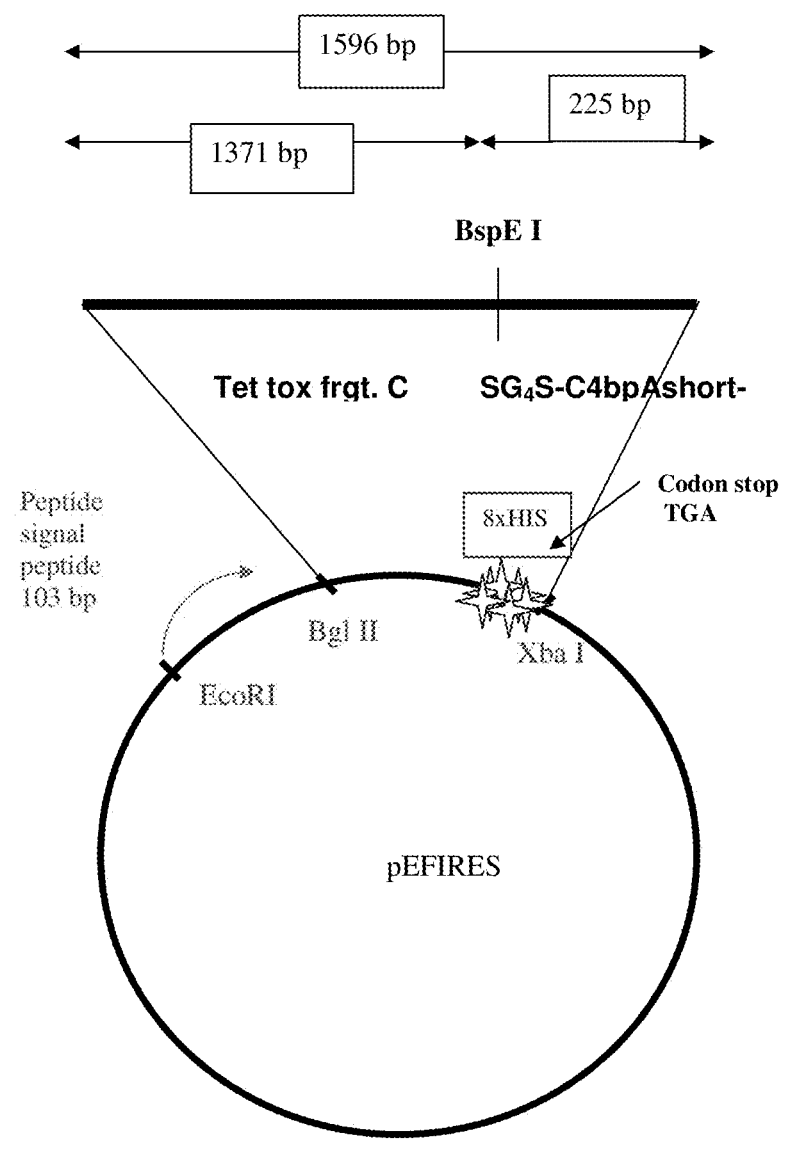

The amplified products of 1371 bp for TTFgC and 225 bp for C4BP were purified by QIAquick PCR Purification Kit protocol (Qiagen, Hilden, Germany) and ligated in pEFIRES-P vector (kindly provided by X. DERVILLEZ, Institute for Biomedical Research Frankfurt, Germany) by T4 DNA ligase (Stratagene, Hwy, USA). The recombinant clones were screened on Luria-Bertani agar containing ampicillin 100 µg/ml. The clones were selected after BglII and XbaI digestion of each plasmid DNA obtained by mini-lysate preparation. One clone was sequenced (Genomexpress, Meylan, France) to confirm the presence of the TTFgC-C4BPα insert and whether it was cloned in frame and was chosen for expression studies (FIG. 1, and sequences SEQ ID NO:1 and NO:2).

2.2 Cloning of the Anti-GPA scFv-C4BPα Construct

The assembled anti-GPA scFv DNA fragment was amplified using forward primer 5'-CGCGAGAGATCTCAGGT-GAAACTGCAGCAG-3' (SEQ ID NO:13) (Eurogentec, Angers, France) and reverse primer 5'-CGCGAGTCCG-GACCGTTTTATTTCCAGCTT-3' (SEQ ID NO:14) (Eurogentec, Angers, France). The restriction sites BglII and BspEI (underlined sequences) were inserted into forward and reverse primers respectively to facilitate anti-GPA scFv subcloning. A 100 µl reaction mixture was prepared, containing 500 ng of DNA, 500 ng of 3' and 5' primers, 16 nM dNTP, 10 mM Tris-HCl (pH 8.3), 50 mM KCl 1.5 mM MgCl$_2$ and 2 U of AmpliTaq DNA polymerase (Perkin-Elmer, Roissy, France), then subjected to 30 cycles of amplification [30 s at 94° C., 45 s at 64° C., 1 min at 72° C.] using a GenAmp PCR System 9600 (Perkin-Elmer). PCR products were analyzed by electrophoresis on a 2% agarose gel. PCR amplification of C4BPα was done as previously described.

The amplified products of 770 bp for anti-GPA scFv and 225 bp for C4BPα were purified by QIAquick PCR Purification Kit protocol (Qiagen, Hilden, Germany) and ligated in pEFIRES-P vector. The ligation product was introduced into *Escherichia coli* and one positive clone was sequenced (Genomexpress, Meylan, France) (FIG. 2, and sequences SEQ ID NO:3 and NO:4).

2.3 Cloning of the Anti-GPA scFv-C4BPβ construct

The assembled anti-GPA scFv DNA fragment was amplified using forward primer 5'-CGCGAGAGATCTCAGGT-GAAACTGCAGCAG-3' (SEQ ID NO:13) (Eurogentec, Angers, France) and reverse primer 5'-CGCGAGGCGGC-CGCCCGTTTTATTTCCAGCTTG-3' (SEQ ID NO:15) (Eurogentec, Angers, France). The restriction sites BglII and NotI (underlined sequences) were inserted into forward and reverse primers respectively to facilitate Anti-GPA scFv subcloning. A 100 µl reaction mixture was prepared, containing 500 ng of DNA, 500 ng of 3' and 5' primers, 16 nM dNTP, 10 mM Tris-HCl (pH 8.3), 50 mM KCl 1.5 mM MgCl$_2$ and 2 U of AmpliTaq DNA polymerase (Perkin-Elmer, Roissy, France), then subjected to 30 cycles of amplification [30 s at 94° C., 45 s at 58° C., 1 min at 72° C.] using a GenAmp PCR System 9600 (Perkin-Elmer).

PCR amplification of C4BPβ was fulfilled by forward primer: 5'-
(SEQ ID NO: 16)
CGCGAG<u>GCGGCCGC</u>ATCCGGAGGCGGTGGCTCG -3'

(Eurogentec, Angers, France) and reverse primer: 5'-CGAGTCTAGATCAGTGATGGTGATGGTGATGGAT-CAACAATTTTGCCTTCAA-3' (SEQ ID NO:17) (Eurogentec, Angers, France). Restriction sites NotI and XbaI (underlined sequences) were inserted into forward and reverse primers respectively to facilitate the C4bpβ subcloning. A 100 µl reaction mixture was prepared, containing 500 ng of DNA, 500 ng of 3' and 5' primers, 16 nM dNTP, 10 mM Tris-HCl (pH 8.3), 50 mM KCl, 1.5 mM MgCl$_2$ and 2 U of AmpliTaq DNA polymerase (Perkin-Elmer, Roissy, France), then subjected to 30 cycles of amplification [30 s at 94° C., 30 s at 61° C., 30 s at 72° C.] using a GenAmp PCR System 9600 (Perkin-Elmer).

PCR products were analyzed by electrophoresis on a 2% agarose gel.

The amplified products of 770 bp for Anti-GPA scFv and 340 bp for C4BPβ were purified by QIAquick PCR Purification Kit protocol (Qiagen, Hilden, Germany) and ligated in pEFIRES-P vector. The ligation product was introduced into *Escherichia coli* and one positive clone was sequenced (Genomexpress, Meylan, France).

2.4 Cloning of the Anti-CEA VHH—C4BPα Construct

DNA of anti-CEA VHH was kindly provided by D. Baty (CNRS, UPR9027, Laboratoire des Systèmes Macromoléculaires, Marseille, France).

The VHH DNA fragment was amplified using forward primer 5'-CGCGAGAGATCTGAGGTGCAGCTGGTG-GAG-3' (SEQ ID NO:18) (Eurogentec, Angers, France) and reverse primer 5'-CGCGAGTCCGGATGAGGAGACAGT-GACCTG-3' (SEQ ID NO:19) (Eurogentec, Angers, France). DNA of anti-CEA VHH was used for PCR amplification. A 100 µl reaction mixture was prepared, containing 500 ng of DNA, 500 ng of 3' and 5' primers, 16 nM dNTP, 10 mM Tris-HCl (pH 8.3), 50 mM KCl 1.5 mM MgCl$_2$ and 2 U of AmpliTaq DNA polymerase (Perkin-Elmer, Roissy, France), then subjected to 30 cycles of amplification [30 s at 94° C., 45 s at 64° C., 1 min at 72° C.] using a GenAmp PCR System 9600 (Perkin-Elmer). PCR products were analyzed by electrophoresis on a 2% agarose gel.

The restriction sites BglII and BspEI (underlined sequences) were inserted into forward and reverse primers respectively to facilitate anti-CEA VHH insert in pEFIRES-P vector. Conditions for PCR amplification of C4BPα were previously described. The amplified products of 360 bp for anti-CEA VHH and 225 bp for C4BPα were by QIAquick PCR Purification Kit protocol (Qiagen, Hilden, Germany) and ligated in pEFIRES-P vector. The ligation product was introduced into *Escherichia coli* and one positive clone was sequenced (Genomexpress, Meylan, France).

2.5 293T Cell Culture and Transfection

Human embryonic kidney cells, 293T (ATCC CRL-11268) were routinely maintained in Dulbecco's modified Eagle Medium with glucose 4500 mg/l, L-glutamine 580 mg/l and sodium pyruvate 110 mg/l (Gibco, Grand Island, USA) supplemented with 10% heat-inactivated fetal calf serum and penicillin/streptomycin/fungizone (1000 U/ml; 1000 µg/ml; 2.5 µg/ml). Cells were grown at 37° C. in a humidified atmosphere of 5% $CO_2$.

Three million and half cells were transfected in a 25 cm² flask with 10 µg of DNA by 20 µl of lipofectamine 2000 (Invitrogen, Carlsbad, USA). Transfected cells were plated in the same medium supplemented with 20 µg/ml puromycin (Sigma, St Louis, USA) to select resistant clones.

Homomultimeric TTFgC-C4BPα, anti-GPA scFv-C4BPα or anti-CEA VHH-C4BPα and Heteromultimeric TTFgC-C4BPα/anti-GPA scFv-C4BPα or TTFgC-C4BPα/anti-CEA VHH-C4BPα secreting clones were screened after limiting dilution by western blotting under reducing conditions.

3 DNA Constructions for SF9 Cell Transfections and Infections 3.1 Cloning of the Anti-GPA scFv-C4BPα and TTFgC-C4BPα Constructs cDNA of anti-GPA-scFv was amplified by PCR using forward

```
primer 5'-
                                      (SEQ ID NO: 20)
CGCGAGCCCGGGGCAGGTGAAACTGCAGCAGTCT-3'
```

(Eurogentec, Angers, France) and reverse

```
primer 5'-
                                      (SEQ ID NO: 21)
CGCGAGGCGGCCGCCCGTTTTATTTCAGCTTGGT-3'
```

(Eurogentec, Angers, France). The restriction sites XmaI and NotI (underlined sequences) were inserted into forward and reverse primers respectively to facilitate anti-GPA scFv subcloning.

PCR amplification of C4BP was fulfilled by forward

```
primer: 5'-
                                      (SEQ ID NO: 22)
CGCGAGGCGGCCGCATCCGGAGGCGGTGGCTCG-3'
```

(Eurogentec, Angers, France) and reverse primer: 5'-CGCGAGAGATCTTATTACAACAATTTTGCCTTC-3' (SEQ ID NO:23) (Eurogentec, Angers, France). Restriction sites NotI and BglII (underlined sequences) were inserted into forward and reverse primers respectively to facilitate C4BPα subcloning. A 100 µl reaction mixture was prepared, containing 500 ng of DNA, 500 ng of 3' and 5' primers, 16 nM dNTP, 10 mM Tris-HCl (pH 8.3), 50 mM KCl, 1.5 mM $MgCl_2$ and 2 U of AmpliTaq DNA polymerase (Perkin-Elmer, Roissy, France), then subjected to 30 cycles of amplification [30 s at 94° C., 30 s at ° C., 30 s at 72° C.] using a GenAmp PCR System 9600 (Perkin-Elmer).

The amplified cDNA of C4BPα product was purified and ligated in pAcGP67C baculovirus transfer vector (PharMingen, San Diego, USA).

Figure 3:
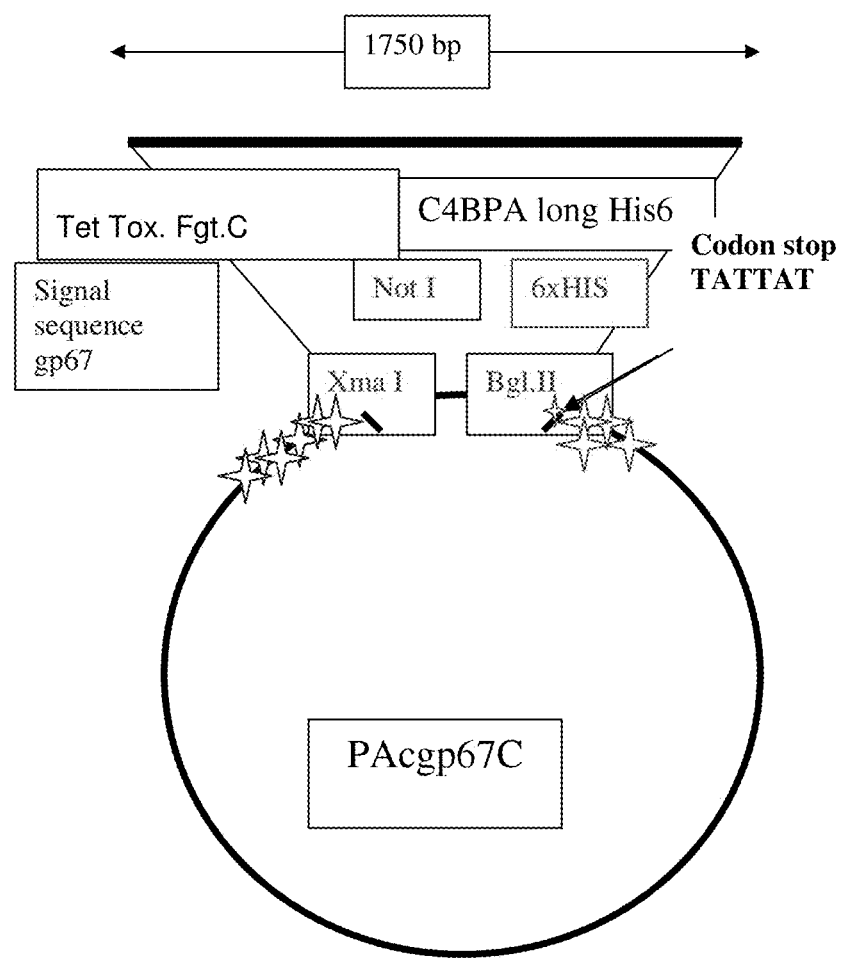
Figure 4:
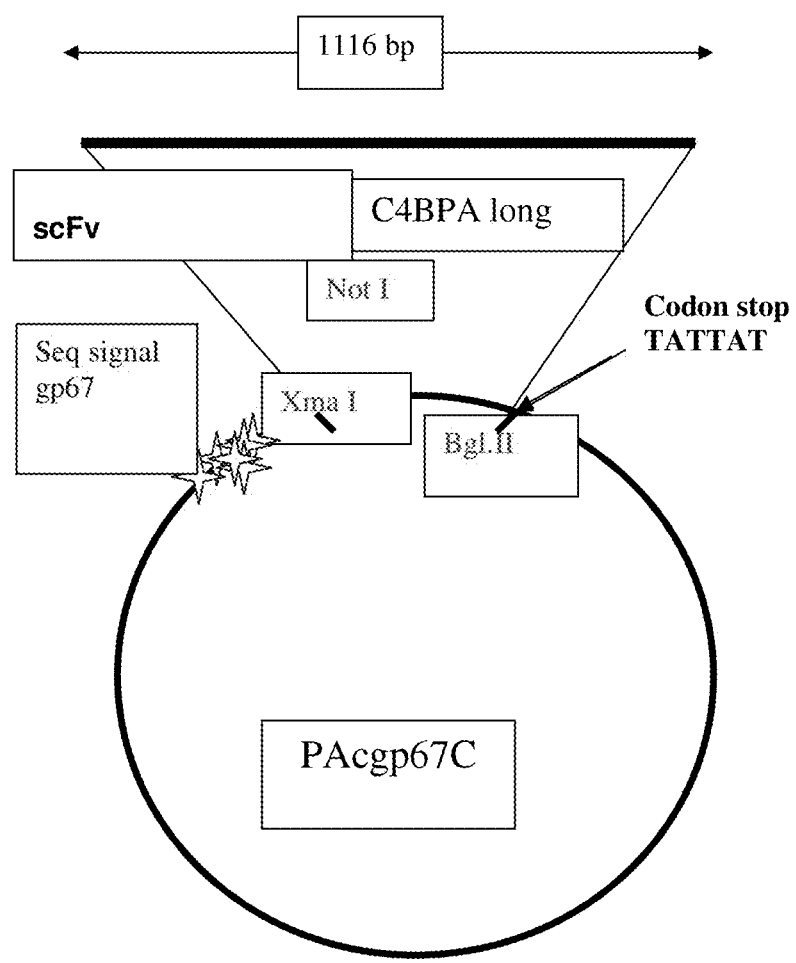

The TTFgC-C4BPα DNA was amplified using forward primer 5'-CGCGAGCCCGGGGCTGGATTGTTGGGTT-GATAATG-3' (SEQ ID NO:24) (Eurogentec, Angers, France) with restriction site (underlined sequence) of XmaI, and the same reverse primer as anti-GPA scFv-C4BPα. The amplified product was ligated in pAcGP67C baculovirus transfer vector. The ligation product was introduced into *Escherichia coli* and one clone was sequenced (Genomexpress, Meylan, France) (FIG. 3, and SEQ ID NO: 5 and NO:6; FIG. 4, SEQ ID NO:7 and NO:8).

3.2 SF9 Cell Culture and Infection

Sf9 cells were cotransfected with viral DNA BaculoGold linearized Baculovirus DNA (Becton Dickinson, Pont de Claix, France) and anti-GPA scFv-C4BPα or TTFgC-C4BPα constructs. All recombinant viruses were isolated from the transfection supernatant through plaque purification and virus stocks were generated by propagating viruses in Sf9 cells and titrated using end-point dilution assays according to the Baculovirus Expression Vector Systems and Insect Cell Culture Techniques Guide (Invitrogen, Cergy Pontoise, France). The presence of the different inserts was verified by PCR.

4 Detection of the Homo and Heteromultimeric Produced Molecules 4.1 Western Blotting Detection TTFgC-C4BPα, anti-GPA scFv-C4BPα or anti-CEA VHH-C4BPα transfected cell supernatants were concentrated 5 fold by using centricon 100 (Millipore, Bedford, USA). Proteins were separated in sodium dodecyl sulfate (SDS)-polyacrylamide gel under reducing conditions and transferred into nitro-cellulose membrane. The presence of the TTFgC-C4BPα ($His_6$) monomers and anti-CEA VHH-C4BPα ($His_6$) were visualised by using a mouse anti-$His_6$ peroxydase antibody (Roche, Indianapolis, USA) used at one unit in PBS (Biomérieux, Marcy l'Étoile, France). Anti-GPA scFv-C4BPα was detected by using a rabbit anti scFv antibody (kindly provided by Dr J. L Teillaud, Unite INSERM U 255, Paris) at 10 µg in 0.1% Tween 20 and 1% milk, PBS.

Heteromultimeric TTFgC-C4BPα/anti-GPA scFv-C4BPα under reducing conditions as previously described.

4.2 Biosynthetic Cell Labelling and Immunoprecipitation

Cells were cultured for 1 night, in RPMI 1640 without cysteine and methionine (Sigma, St Louis, USA) supplemented with 10% heat-inactivated FCS, glutamine (2 mM), penicillin/streptomycin/fungizone (1000 U/ml; 1000 µg/ml; 2.5 µg/ml), and 50 µCi of [$^{35}$S]methionine cysteine (Amersham Biosciences, Buckinghamshire, England). Twenty five microliters of goat anti-mouse IgG-coated magnetic beads (Dynal, Oslo, Norway) were washed three times with 0.1% BSA PBS (Sigma, St Louis, USA) then incubated with 1 µg of anti-tetanus toxin fragment C (Roche, Indianapolis, USA) for 1 night at 4° C. Beads were washed three times with 0.1% BSA PBS. Transfected cell culture supernatants were incubated with beads for 1 night at 4° C. Washed beads were then resuspended in SDS-PAGE sample buffer for electrophoresis. Reduced and unreduced immunoprecipitates were subjected to electrophoresis in a 5% SDS acrylamide gel.

5 Analysis of the Heteromultimeric Molecule Activity 5.1 Assessment of the Fixation of Heteromultimeric Proteins 5.1.1 Fixation of TTFgC-C4BPα/anti-GPA scFv-C4BPα on Erythrocytes a. Direct Hemagglutination Sepharose columns were purchased from DiaMed (Paris, France). Twenty microliters of a 2.5% suspension of E were incubated for 45 minutes at 37° C. with 50 µl of supernatant of transfected cells. Agglutination was then assessed in columns after a 1,000 g centrifugation for 10 minutes at room temperature.

b. Flow Cytometry Assay

TTFgC-C4BPα/anti-GPA scFv-C4BPα binding on erythrocytes was analysed by flow cytometry. Washed E were incubated for 1 hour at room temperature with transfected cells supernatant then washed three times with 1% BSA PBS. Human serum or 1 μg of anti-tetanus toxin fragment C (Roche, Indianapolis, USA) were added for 45 minutes at room temperature. Erythrocytes were washed twice, and then 1 μg of goat anti-Human Ig (H+L) biotinylated antibody (Southern Biotechnology Associates, Birmingham, USA) or anti-mouse Ig biotinylated antibody (Amersham Biosciences, Buckinghamshire, UK) were added before 1.5 μg of Streptavidin R-Phycoerythrin conjugated antibody (tebu-bio, Burlingame, USA) conjugated detection system. Flow cytometry of stained cells was performed on a FACStar$^{Plus}$ apparatus (Becton Dickinson, Mountain View, Calif., USA). At least 10,000 events for each sample were collected. Mean fluorescence channel was used to quantify the staining of each sample. TTFgC-C4BPα/anti-GPA scFv-C4BPα distribution pattern was analyzed using fluorescence microscopy.

5.1.2 Fixation of TTFgC-C4BPα/Anti-CEA VHH-C4BPα on LS174T Cells Assessed by Flow Cytometry TTFgC-C4BPα/anti-CEA VHH-C4BPα binding to LS174T cells (ATCC CCL 188) was analysed by flow cytometry. Washed LS174T cells were incubated with transfected cell supernatant for 90 minutes at 4° C. then washed three times with 0.5% BSA PBS. 1 μg of anti-tetanus toxin fragment C or 3.3 μg monoclonal anti-c-myc (mouse IgG1 isotype) (Sigma, Saint Louis, USA) for monomeric c-myc tagged anti-CEA VHH provided by Dr. Baty, were added for 45 minutes at room temperature as positive control.

LS174T cells were washed twice, and then anti-mouse Ig biotinylated antibody (Amersham Biosciences, Buckinghamshire, England) was added before R-Phycoerythrin conjugated Streptavidin detection system.

5.2 Complement (C) Fixation Tests 5.2.1 Assessment of C Activation by TTFgC-C4BPα/Anti-GPA scFv-C4BPα Using Hemolytic Assay Fifteen microliters of 2.5% suspension of E were incubated with 200 μl of 5 fold concentrated transfected cell supernatant at room temperature for 1 hour in 0.24 M glycin, 3 mM sodium phosphate (pH 6.8), 31 mM NaCl, low ionic strength saline buffer including 0.15 mM $Ca^{2+}$, and 0.5 mM $Mg^{2+}$.

After 5 minutes of 160 g centrifugation at room temperature, supernatant was removed and 100 μl of serum of a healthy individual who gave an informed consent for research used, recently vaccinated against tetanus were then added (E were also from the same person). Monoclonal antibody (MoAb) against glycophorin A (R18) was used as positive control. After 1 hour incubation at 37° C. and a quick cooling in an ice-water bath, tubes were centrifuged for 10 minutes at 160 g, then the 630-405 nm optical density of the supernatants was determined using a microplate reader (SLT, Labinstruments, Vietech, St Bonnet De Mure, France).

5.2.2 Assessment of C Activation by TTFgC-C4BPα/Anti-GPA scFv-C4BPα Using Flow Cytometry Analysis Fifteen microliters of 2.5% suspension E (O Rh(D)-negative) was added to 100 μl of transfected cell supernatant for 1 hour at room temperature. After centrifugation as previously described, supernatant is removed and 100 μl of heat inactivated serum of recently vaccinated person against tetanus were added. Incubation at room temperature for 1 hour was followed by 2 times washing with 1% BSA PBS. Fifty microliters of Human C5-deficient serum, two fold diluted in low ionic strength saline buffer including 0.15 mM $Ca^{2+}$ and 0.5 mM $Mg^{2+}$ was added, and the mixture was incubated for 1 hour at 37° C. Human C3b deposits were revealed by fluorescein-labeled goat antiserum against human C3b (Immunotech, Marseille, France) and C4d by a biotinylated monoclonal anti-Human C4d (Quidel, San Diego, USA) followed by Streptavidin R-Phycoerythrin conjugated detection system. E were washed twice, stabilized in 0.37% formaldehyde PBS buffer, and then analyzed on a FACStar Plus (Becton Dickinson). C4d and C3b distribution pattern were analyzed using fluorescence microscopy.

Results

The results obtained with the Baculovirus expression system were similar to those of the 293T expression system.

1 Detection of Homo and Heteromultimeric Recombinant Proteins Secreted

The production of homomultimeric and heteromultimeric recombinant proteins was characterized by Western blotting and radioactive labeling.

1.1 Homomultimeric Molecules 1.1.1 TTFgC-C4BPα Protein

TTFgC-C4BPα monomers were identified by using an anti-His immunoblotting detection. GFP-$(His)_6$ was used as positive control; Its molecular weight was 32 Kda. The apparent molecular weight of TTFgC-C4BPα monomers was assessed from SDS-PAGE under reducing conditions and was found to be 82 Kda.

Multivalent TTFgC recombinant proteins were obtained using C4BPα multimerizing fragments fused at the C-terminal end of the molecule. They were soluble and stable in culture supernatant of the selected clones.

$^{35}S$ amino-acid labeling experiments showed that two molecular species of more than 500 KDa apparent molecular weight on SDS-PAGE analysis were secreted. This pattern is compatible with a 6 and 7 valence multimers, a counterpart of the physiological pattern of C4BPα multimers that consists mainly of octamers (656 KDa) together with a few heptamers (574 KDa) and hexamers (492 KDa).

1.1.2 Anti-GPA scFv-C4BPα Protein

A single molecular species of anti-GPA scFv-C4BPα protein with an apparent molecular weight more than 210 KDa was detected by SDS-PAGE analysis in native conditions. This multimer was an heptamer (245 KDa). In reducing conditions, the apparent molecular weight of the monomer was 35 Kda.

1.1.3 Anti-CEA VHH-C4BPα Protein

Anti-CEA VHH-C4BPα monomers were identified by using an anti-His immunoblotting detection. The apparent molecular weight was assessed from SDS-PAGE under reducing conditions and was found to be 22 Kda.

1.2 Heteromultimeric Molecules 1.2.1 TTFgC-C4BPα/Anti-GPA scFv-C4BPα Recombinant Proteins Under reducing conditions, TTFgC-C4BPα and anti-GPA scFv-C4BPα monomers were identified using anti-His immunoblotting detection. Their molecular weights were found to be 82 KDa and 35 KDa respectively.

Heteromultimeric TTFgC-C4BPα/anti-GPA scFv-C4BPα recombinant protein were detected by radioactive labeling in nonreducing conditions. After five days of exposure several valences of TTFgC-C4BPα/anti-GPA scFv-C4BPα with an apparent molecular weight of more than 300 KDa can be visualized. Two main valences were detected with 2 hours of exposure. Multivalent TTFgC recombinant proteins were used as positive control.

1.2.2 TTFgC-C4Bpα/Anti-CEA VHH-C4BPα Recombinant Proteins

TTFgC-C4BPα and anti-CEA VHH-C4BPα monomers were identified using anti-His immunoblotting detection under reducing conditions; their molecular weights were found to be 82 KDa and 22 KDa respectively.

Heteromultimeric TTFgC-C4BPα/anti-CEA VHH-C4BPα molecules were detected by radioactive labeling in nonreducing conditions and showed three main valences with apparent molecular weight of more than 400 KDa. Multivalent TTFgC recombinant proteins and heteromultimeric TTFgC-C4BPα/anti-GPA scFv-C4BPα recombinant molecules were used as positive control.

Figure 5:
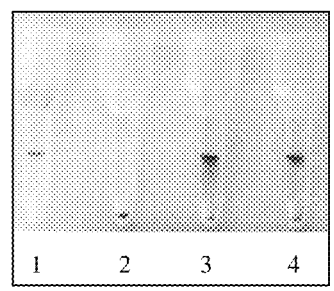
Figure 6:
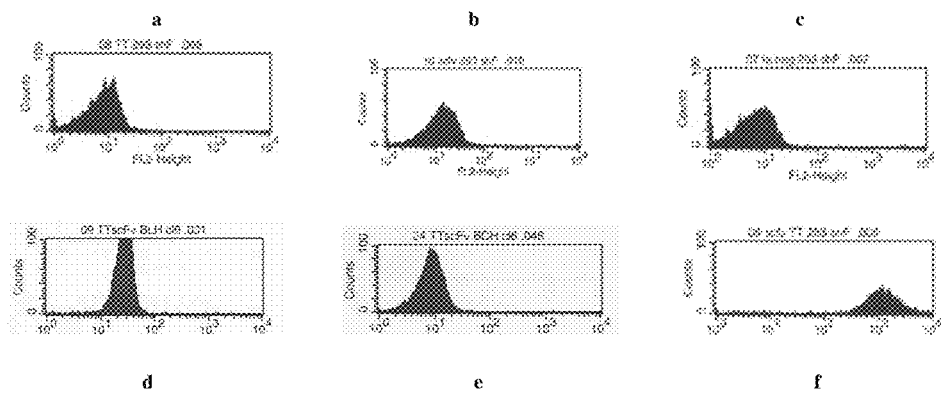
Figure 7:
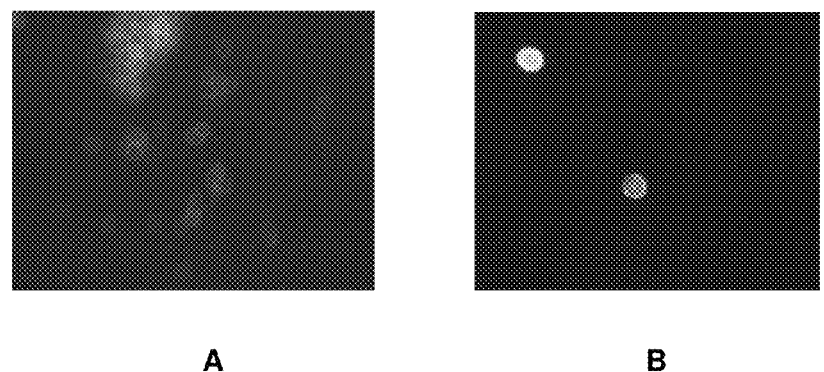
Figure 8:
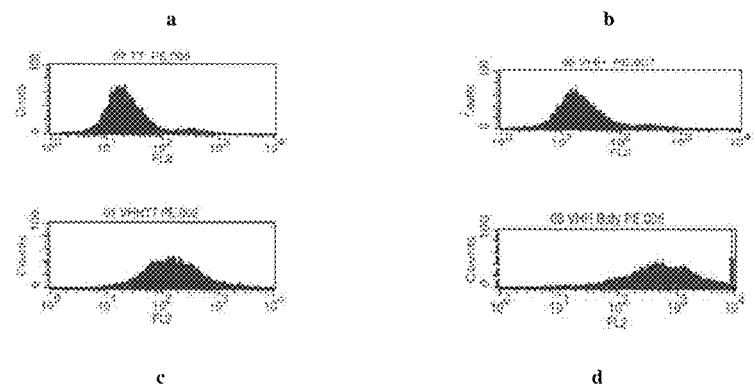
Figure 9:
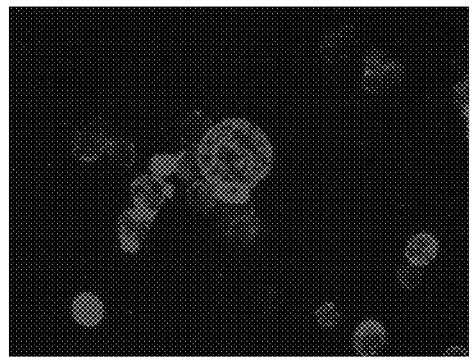
Figure 10:
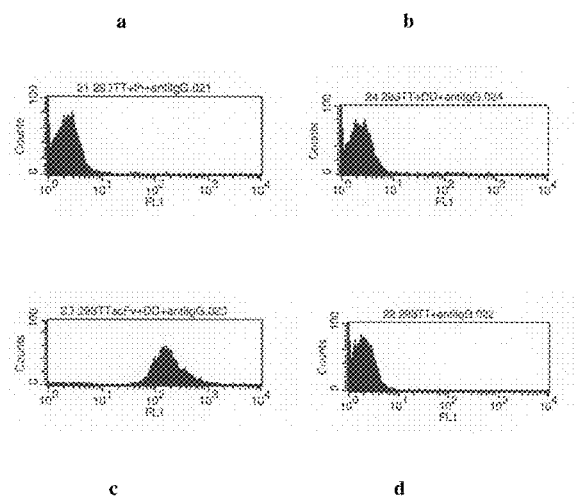
Figure 11:
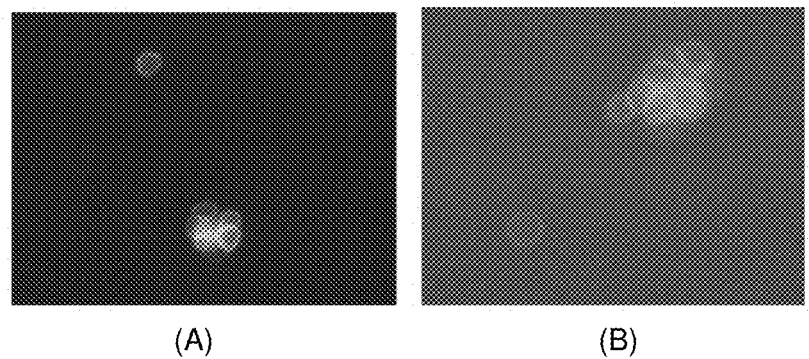
Figure 12:
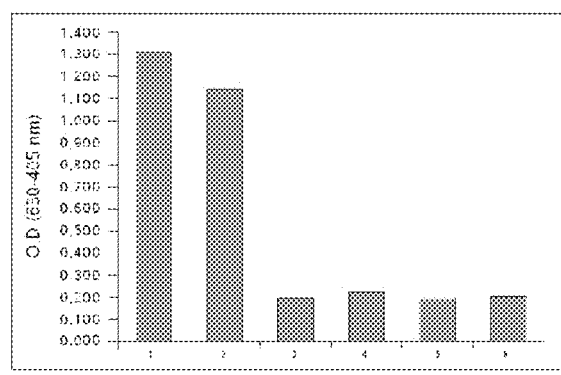

2 Analysis of Heteromultimeric Molecule Activity
2.1 Analysis of the Fixation of Heteromultimeric Molecules to the Cell Membrane Surface
2.1.1 Analysis of the Fixation of TTFgC-C4BPα/Anti-GPA scFv-C4BPα and TTFgC-C4BPα/Anti-GPA scFv-C4BPβ Molecule at the E Membrane Surface a. Direct Hemagglutination Anti-GPA ScFv-C4BPα and TTFgC-C4BPα/anti-GPA ScFv-C4BPα directly agglutinated erythrocytes as R18 natif antibody (FIG. 5). Supernatants are still functional by direct hemagglutination after 6 months at 4° C., this proved stability of these recombinant heteromultimers.

b Flow Cytometry

To demonstrate the TTFgC-C4BPα/anti-GPA scFv-C4BPα and TTFgC-C4BPα/anti-GPA scFv-C4BPβ specific binding at the erythrocyte membrane surface quantitative flow cytometry analysis with supernatants of transfected 293T cells were performed.

Multimeric TTFgC-C4BPα/anti-GPA scFv-C4BPα (FIG. 6.*f*) as well as TTFgC-C4BPα/anti-GPA scFv-C4BPβ molecule (FIG. 6.*d*; FIG. 6.*e*) were able to bind at the erythrocyte membrane surface.

Homomultimeric TTFgC-C4BPα and homomultimeric anti-GPA scFv-C4BPα were used as negative controls:

- homomultimeric TTFgC-C4BPα was not able to bind at the E (FIG. 6.*a*).
- homomultimeric anti-GPA scFv-C4BPα was attached to E but not detected by flow cytometry as not revealed by anti-TTFgC (FIG. 6.*b*).

c Fluorescence Microscopy

The distribution of heteromultimers to the E membrane surface was analyzed by using fluorescence microscopy and was homogeneous (FIG. 3).

2.1.2 Analysis of TTFgC-C4BPα/Anti-CEA VHH-C4BPα Molecule Binding at the LS174T Cell Membrane Surface a Flow Cytometry To demonstrate the TTFgC-C4BPα/anti-CEA VHH-C4BPα specific binding at the LS174T membrane surface; quantitative flow cytometry analysis with supernatants of transfected 293T cells were performed.

Monomeric anti-CEA VHH-c-myc and TTFgC-C4BPα/anti-CEA VHH-C4BPα heteromultimeric molecules were detected at the LS174T membrane surface (FIGS. 8.*d* and 8.*c*).

Homomultimeric VHH-C4BPα molecules were attached to the LS174T cells surface but not detected by flow cytometry because not revealed by anti-TTFgC (FIG. 8.*b*).

b Fluorescence Microscopy

The distribution of heteromultimeric TTFgC-C4BPα/anti-CEA VHH-C4BPα to the LS174T membrane surface was analyzed using fluorescence microscopy and was heterogeneous (FIG. 9).

2.2 Analysis of Complement Activation by TTFgC-C4BPα/Anti-GPA scFv-C4BPα Molecules The ability of heteromultimeric TTFgC-C4BPα/anti-GPA scFv-C4BPα molecules to activate the complement was tested.

Erythrocytes were incubated with a C5-deficient serum in presence of TTFgC-C4BPα/anti-GPA scFv-C4BPα constructs transfected 293T cell supernatant. The C5-deficiency of this serum stops the complement cascade and E are not lysed. C4d binding was detected at the erythrocyte membrane surface by flow cytometry and fluorescence microscopy (FIG. 10 and FIG. 11B) as well as C3b (Data not shown and FIG. 11A). Erythrocytes from an healthy individual, recently vaccinated against tetanus were incubated with his serum, in presence of TTFgC-C4BPα/anti-GPA scFv-C4BPα transfected cell supernatant. Anti-tetanus toxin antibodies present in the serum are able to link to the TTFgC portion of the TTFgC-C4BPα/anti-GPA scFv-C4BPα heteromultimeric molecules attached at the erythrocyte surface. Erythrocytes have been opsonized and complement activation cascade started. Under these conditions the final membrane attack pathway of complement could be activated and lysed the erythrocytes.

FIG. 12 showed that heteromultimeric molecules induce the erythrocyte lysis at 87% whereas homomultimeric molecules are not able to induce erythrocyte lysis at all.

The invention claimed is:

1. A method of killing undesired target tumor cells in a patient, the method comprising administering to a patient in need thereof an effective amount of a multimeric protein construct, the multimeric protein construct comprising a multimerizing scaffold bearing (i) at least one targeting moiety that is capable of binding to the target tumor cells, and (ii) at least two effector immunogenic moieties that are non-toxic by themselves, wherein the multimerizing scaffold comprises the C-terminal part of the alpha chain of C4BP protein, the C-terminal part of the beta chain of C4BP protein, or a multimerizing fragment thereof the at least two effector immunogenic moieties are each fragment C of tetanus toxin (TTFgC); the at least one targeting moiety is an antibody or a binding fragment thereof against a tumor-associated antigen of the target tumor cells; and the multimeric protein construct redirects an anti-tetanus immune response that was pre-existing in the patient, toward the target tumor cells.

2. The method of claim 1, wherein the multimerizing scaffold bears at least five effector immunogenic moieties that are non-toxic by themselves.

3. The method of claim 1, wherein the multimerizing scaffold comprises the C-terminal part of the alpha chain of C4BP and the C-terminal part of the beta chain of C4BP.

4. The method of claim 1, wherein the patient is naturally vaccinated against tetanus.

5. The method of claim 1, wherein the patient was previously subjected to a vaccination against tetanus.

* * * * *

SEQUENCE LISTING

```
<160> NUMBER OF SEQ ID NOS: 24

<210> SEQ ID NO 1
<211> LENGTH: 1593
<212> TYPE: DNA
<213> ORGANISM: artificial sequence
<220> FEATURE:
<223> OTHER INFORMATION: TTFgC-C4BPalpha insert for transfection in 293T
      cells
<220> FEATURE:
<221> NAME/KEY: CDS
<222> LOCATION: (1)..(1593)

<400> SEQUENCE: 1 gat ctg gcc cag ccg gcc ctg gat tgt tgg gtt gat aat gaa gaa gat      48
Asp Leu Ala Gln Pro Ala Leu Asp Cys Trp Val Asp Asn Glu Glu Asp
1               5                   10                  15
```

| | | |
|---|---|---|
| ata gat gtt ata tta aaa aag agt aca att tta aat tta gat att aat<br>Ile Asp Val Ile Leu Lys Lys Ser Thr Ile Leu Asn Leu Asp Ile Asn<br>20 25 30 | | 96 |
| aat gat att ata tca gat ata tct ggg ttt aat tca tct gta ata aca<br>Asn Asp Ile Ile Ser Asp Ile Ser Gly Phe Asn Ser Ser Val Ile Thr<br>35 40 45 | | 144 |
| tat cca gat gct caa ttg gtg ccc gga ata aat ggc aaa gca ata cat<br>Tyr Pro Asp Ala Gln Leu Val Pro Gly Ile Asn Gly Lys Ala Ile His<br>50 55 60 | | 192 |
| tta gta aac aat gaa tct tct gaa gtt ata gtg cat aaa gct atg gat<br>Leu Val Asn Asn Glu Ser Ser Glu Val Ile Val His Lys Ala Met Asp<br>65 70 75 80 | | 240 |
| att gaa tat aat gat atg ttt aat aat ttt acc gtt agc ttt tgg ttg<br>Ile Glu Tyr Asn Asp Met Phe Asn Asn Phe Thr Val Ser Phe Trp Leu<br>85 90 95 | | 288 |
| agg gtt cct aaa gta tct gct agt cat tta gaa caa tat ggc aca aat<br>Arg Val Pro Lys Val Ser Ala Ser His Leu Glu Gln Tyr Gly Thr Asn<br>100 105 110 | | 336 |
| gag tat tca ata att agc tct atg aaa aaa cat agt cta tca ata gga<br>Glu Tyr Ser Ile Ile Ser Ser Met Lys Lys His Ser Leu Ser Ile Gly<br>115 120 125 | | 384 |
| tct ggt tgg agt gta tca ctt aaa ggt aat aac tta ata tgg act tta<br>Ser Gly Trp Ser Val Ser Leu Lys Gly Asn Asn Leu Ile Trp Thr Leu<br>130 135 140 | | 432 |
| aaa gat tcc gcg gga gaa gtt aga caa ata act ttt agg gat tta cct<br>Lys Asp Ser Ala Gly Glu Val Arg Gln Ile Thr Phe Arg Asp Leu Pro<br>145 150 155 160 | | 480 |
| gat aaa ttt aat gct tat tta gca aat aaa tgg gtt ttt ata act att<br>Asp Lys Phe Asn Ala Tyr Leu Ala Asn Lys Trp Val Phe Ile Thr Ile<br>165 170 175 | | 528 |
| act aat gat aga tta tct tct gct aat ttg tat ata aat gga gta ctt<br>Thr Asn Asp Arg Leu Ser Ser Ala Asn Leu Tyr Ile Asn Gly Val Leu<br>180 185 190 | | 576 |
| atg gga agt gca gaa att act ggt tta gga gct att aga gag gat aat<br>Met Gly Ser Ala Glu Ile Thr Gly Leu Gly Ala Ile Arg Glu Asp Asn<br>195 200 205 | | 624 |
| aat ata aca tta aaa cta gat aga tgt aat aat aat aat caa tac gtt<br>Asn Ile Thr Leu Lys Leu Asp Arg Cys Asn Asn Asn Asn Gln Tyr Val<br>210 215 220 | | 672 |
| tct att gat aaa ttt agg ata ttt tgc aaa gca tta aat cca aaa gag<br>Ser Ile Asp Lys Phe Arg Ile Phe Cys Lys Ala Leu Asn Pro Lys Glu<br>225 230 235 240 | | 720 |
| att gaa aaa tta tac aca agt tat tta tct ata acc ttt tta aga gac<br>Ile Glu Lys Leu Tyr Thr Ser Tyr Leu Ser Ile Thr Phe Leu Arg Asp<br>245 250 255 | | 768 |
| ttc tgg gga aac cct tta cga tat gat aca gaa tat tat tta ata cca<br>Phe Trp Gly Asn Pro Leu Arg Tyr Asp Thr Glu Tyr Tyr Leu Ile Pro<br>260 265 270 | | 816 |
| gta gct tct agt tct aaa gat gtt caa ttg aaa aat ata aca gat tat<br>Val Ala Ser Ser Ser Lys Asp Val Gln Leu Lys Asn Ile Thr Asp Tyr<br>275 280 285 | | 864 |
| atg tat ttg aca aat gcg cca tcg tat act aac gga aaa ttg aat ata<br>Met Tyr Leu Thr Asn Ala Pro Ser Tyr Thr Asn Gly Lys Leu Asn Ile<br>290 295 300 | | 912 |
| tat tat aga agg tta tat aat gga cta aaa ttt att ata aaa aga tat<br>Tyr Tyr Arg Arg Leu Tyr Asn Gly Leu Lys Phe Ile Ile Lys Arg Tyr<br>305 310 315 320 | | 960 |
| aca cct aat aat gaa ata gat tct ttt gtt aaa tca ggt gat ttt att<br>Thr Pro Asn Asn Glu Ile Asp Ser Phe Val Lys Ser Gly Asp Phe Ile<br>325 330 335 | | 1008 |

```
aaa tta tat gta tca tat aac aat aat gag cac att gta ggt tat ccg      1056
Lys Leu Tyr Val Ser Tyr Asn Asn Asn Glu His Ile Val Gly Tyr Pro
            340                 345                 350 aaa gat gga aat gcc ttt aat aat ctt gat aga att cta aga gta ggt      1104
Lys Asp Gly Asn Ala Phe Asn Asn Leu Asp Arg Ile Leu Arg Val Gly
        355                 360                 365 tat aat gcc cca ggt atc cct ctt tat aaa aaa atg gaa gca gta aaa      1152
Tyr Asn Ala Pro Gly Ile Pro Leu Tyr Lys Lys Met Glu Ala Val Lys
370                 375                 380 ttg cgt gat tta aaa acc tat tct gta caa ctt aaa tta tat gat gat      1200
Leu Arg Asp Leu Lys Thr Tyr Ser Val Gln Leu Lys Leu Tyr Asp Asp
385                 390                 395                 400 aaa aat gca tct tta gga cta gta ggt acc cat aat ggt caa ata ggc      1248
Lys Asn Ala Ser Leu Gly Leu Val Gly Thr His Asn Gly Gln Ile Gly
                405                 410                 415 aac gat cca aat agg gat ata tta att gca agc aac tgg tac ttt aat      1296
Asn Asp Pro Asn Arg Asp Ile Leu Ile Ala Ser Asn Trp Tyr Phe Asn
            420                 425                 430 cat tta aaa gat aaa att tta gga tgt gat tgg tac ttt gta cct aca      1344
His Leu Lys Asp Lys Ile Leu Gly Cys Asp Trp Tyr Phe Val Pro Thr
        435                 440                 445 gat gaa gga tgg aca aat gat tcc gga ggc ggt ggc tcg acc gga tgg      1392
Asp Glu Gly Trp Thr Asn Asp Ser Gly Gly Gly Gly Ser Thr Gly Trp
450                 455                 460 gag acc ccc gaa ggc tgt gaa caa gtg ctc aca ggc aaa aga ctc atg      1440
Glu Thr Pro Glu Gly Cys Glu Gln Val Leu Thr Gly Lys Arg Leu Met
465                 470                 475                 480 cag tgt ctc cca aac cca gag gat gtg aaa atg gcc ctg gag gta tat      1488
Gln Cys Leu Pro Asn Pro Glu Asp Val Lys Met Ala Leu Glu Val Tyr
                485                 490                 495 aag ctg tct ctg gaa att gaa caa ctg gaa cta cag aga gac agc gca      1536
Lys Leu Ser Leu Glu Ile Glu Gln Leu Glu Leu Gln Arg Asp Ser Ala
            500                 505                 510 aga caa tcc act ttg gat aaa gaa cta atc cac cac cat cac cat cac      1584
Arg Gln Ser Thr Leu Asp Lys Glu Leu Ile His His His His His His
        515                 520                 525 cat cac tga                                                          1593
His His
    530

<210> SEQ ID NO 2
<211> LENGTH: 530
<212> TYPE: PRT
<213> ORGANISM: artificial sequence
<220> FEATURE:
<223> OTHER INFORMATION: Synthetic Construct

<400> SEQUENCE: 2

Asp Leu Ala Gln Pro Ala Leu Asp Cys Trp Val Asp Asn Glu Glu Asp
1               5                   10                  15

Ile Asp Val Ile Leu Lys Lys Ser Thr Ile Leu Asn Leu Asp Ile Asn
            20                  25                  30

Asn Asp Ile Ile Ser Asp Ile Ser Gly Phe Asn Ser Ser Val Ile Thr
        35                  40                  45

Tyr Pro Asp Ala Gln Leu Val Pro Gly Ile Asn Gly Lys Ala Ile His
    50                  55                  60

Leu Val Asn Asn Glu Ser Ser Glu Val Ile Val His Lys Ala Met Asp
65                  70                  75                  80

Ile Glu Tyr Asn Asp Met Phe Asn Asn Phe Thr Val Ser Phe Trp Leu
                85                  90                  95
```

```
Arg Val Pro Lys Val Ser Ala Ser His Leu Glu Gln Tyr Gly Thr Asn
            100                 105                 110
Glu Tyr Ser Ile Ile Ser Ser Met Lys Lys His Ser Leu Ser Ile Gly
            115                 120                 125
Ser Gly Trp Ser Val Ser Leu Lys Gly Asn Asn Leu Ile Trp Thr Leu
        130                 135                 140
Lys Asp Ser Ala Gly Glu Val Arg Gln Ile Thr Phe Arg Asp Leu Pro
145                 150                 155                 160
Asp Lys Phe Asn Ala Tyr Leu Ala Asn Lys Trp Val Phe Ile Thr Ile
                165                 170                 175
Thr Asn Asp Arg Leu Ser Ser Ala Asn Leu Tyr Ile Asn Gly Val Leu
            180                 185                 190
Met Gly Ser Ala Glu Ile Thr Gly Leu Gly Ala Ile Arg Glu Asp Asn
        195                 200                 205
Asn Ile Thr Leu Lys Leu Asp Arg Cys Asn Asn Asn Gln Tyr Val
            210                 215                 220
Ser Ile Asp Lys Phe Arg Ile Phe Cys Lys Ala Leu Asn Pro Lys Glu
225                 230                 235                 240
Ile Glu Lys Leu Tyr Thr Ser Tyr Leu Ser Ile Thr Phe Leu Arg Asp
                245                 250                 255
Phe Trp Gly Asn Pro Leu Arg Tyr Asp Thr Glu Tyr Tyr Leu Ile Pro
            260                 265                 270
Val Ala Ser Ser Lys Asp Val Gln Leu Lys Asn Ile Thr Asp Tyr
        275                 280                 285
Met Tyr Leu Thr Asn Ala Pro Ser Tyr Thr Asn Gly Lys Leu Asn Ile
        290                 295                 300
Tyr Tyr Arg Arg Leu Tyr Asn Gly Leu Lys Phe Ile Ile Lys Arg Tyr
305                 310                 315                 320
Thr Pro Asn Asn Glu Ile Asp Ser Phe Val Lys Ser Gly Asp Phe Ile
                325                 330                 335
Lys Leu Tyr Val Ser Tyr Asn Asn Glu His Ile Val Gly Tyr Pro
            340                 345                 350
Lys Asp Gly Asn Ala Phe Asn Asn Leu Asp Arg Ile Leu Arg Val Gly
        355                 360                 365
Tyr Asn Ala Pro Gly Ile Pro Leu Tyr Lys Lys Met Glu Ala Val Lys
370                 375                 380
Leu Arg Asp Leu Lys Thr Tyr Ser Val Gln Leu Lys Leu Tyr Asp Asp
385                 390                 395                 400
Lys Asn Ala Ser Leu Gly Leu Val Gly Thr His Asn Gly Gln Ile Gly
                405                 410                 415
Asn Asp Pro Asn Arg Asp Ile Leu Ile Ala Ser Asn Trp Tyr Phe Asn
            420                 425                 430
His Leu Lys Asp Lys Ile Leu Gly Cys Asp Trp Tyr Phe Val Pro Thr
        435                 440                 445
Asp Glu Gly Trp Thr Asn Asp Ser Gly Gly Gly Ser Thr Gly Trp
        450                 455                 460
Glu Thr Pro Glu Gly Cys Glu Gln Val Leu Thr Gly Lys Arg Leu Met
465                 470                 475                 480
Gln Cys Leu Pro Asn Pro Glu Asp Val Lys Met Ala Leu Glu Val Tyr
                485                 490                 495
Lys Leu Ser Leu Glu Ile Glu Gln Leu Glu Leu Gln Arg Asp Ser Ala
            500                 505                 510
```

```
Arg Gln Ser Thr Leu Asp Lys Glu Leu Ile His His His His His
        515                 520                 525
His His
    530

<210> SEQ ID NO 3
<211> LENGTH: 1137
<212> TYPE: DNA
<213> ORGANISM: artificial sequence
<220> FEATURE:
<223> OTHER INFORMATION: anti-GPA scFv-C4BPalpha insert for transfection
      in 293T cells
<220> FEATURE:
<221> NAME/KEY: CDS
<222> LOCATION: (52)..(1137)

<400> SEQUENCE: 3
cagttcaatt acagctctta aggctagagt acttattacg actcactata g gct agc          57
                                                         Ala Ser
                                                           1 ctc gag aat tca ccg gtc gcc gcc atg ggc gcc ggc gcc acc ggc cgc         105
Leu Glu Asn Ser Pro Val Ala Ala Met Gly Ala Gly Ala Thr Gly Arg
          5                  10                  15 gcc atg gac ggc ccc cgc ctg ctg ctg ctg ctg ctg ggc gtg agc             153
Ala Met Asp Gly Pro Arg Leu Leu Leu Leu Leu Leu Leu Gly Val Ser
 20                  25                  30 ctg ggc ggc gcc aga tct cag gtg aaa ctg cag cag tca ggg gga ggc         201
Leu Gly Gly Ala Arg Ser Gln Val Lys Leu Gln Gln Ser Gly Gly Gly
 35                  40                  45                  50 tta gtg cag cct gga ggg tcc ctg aaa ctc tcc tgt gca gcc tct gga         249
Leu Val Gln Pro Gly Gly Ser Leu Lys Leu Ser Cys Ala Ala Ser Gly
                 55                  60                  65 ttc act ttc agt agc tat ggc atg tct tgg ttt cgc cag act cca gac         297
Phe Thr Phe Ser Ser Tyr Gly Met Ser Trp Phe Arg Gln Thr Pro Asp
             70                  75                  80 aag agg ctg gag ttg gtc gca atc att aat agt aat ggt ggt act acc         345
Lys Arg Leu Glu Leu Val Ala Ile Ile Asn Ser Asn Gly Gly Thr Thr
         85                  90                  95 tat tat cca gac agt gtg aag ggc cga ttc acc atc tcc aga gac aat         393
Tyr Tyr Pro Asp Ser Val Lys Gly Arg Phe Thr Ile Ser Arg Asp Asn
    100                 105                 110 gcc aag aac acc ctg tac ctg caa atg agc agt ctg aag tct gag gac         441
Ala Lys Asn Thr Leu Tyr Leu Gln Met Ser Ser Leu Lys Ser Glu Asp
115                 120                 125                 130 aca gcc atg tat tac tgt gca aga gga gga ggg aga tgg tta ctg gac         489
Thr Ala Met Tyr Tyr Cys Ala Arg Gly Gly Gly Arg Trp Leu Leu Asp
                135                 140                 145 tac tgg ggc caa ggg acc acg gtc acc gtc tcc tca ggt gga ggc ggg         537
Tyr Trp Gly Gln Gly Thr Thr Val Thr Val Ser Ser Gly Gly Gly Gly
            150                 155                 160 tca ggc gga ggt ggc tct ggc ggt ggc gga tcg gac atc gag ctc act         585
Ser Gly Gly Gly Gly Ser Gly Gly Gly Gly Ser Asp Ile Glu Leu Thr
        165                 170                 175 cag tct cca tca tct ctg gct gtg tct gca gga gaa aag gtc act atg         633
Gln Ser Pro Ser Ser Leu Ala Val Ser Ala Gly Glu Lys Val Thr Met
    180                 185                 190 agc tgt aag tcc agt caa agt gtt tta tac agt tca aat cag aag aac         681
Ser Cys Lys Ser Ser Gln Ser Val Leu Tyr Ser Ser Asn Gln Lys Asn
195                 200                 205                 210 tac ttg gcc tgg tac cag cag aaa cca ggg cag tct cct aaa ctg ctg         729
Tyr Leu Ala Trp Tyr Gln Gln Lys Pro Gly Gln Ser Pro Lys Leu Leu
                215                 220                 225
```

```
atc tac tgg gca tcc act agg gaa tct ggt gtc cct gat cgc ttc aca      777
Ile Tyr Trp Ala Ser Thr Arg Glu Ser Gly Val Pro Asp Arg Phe Thr
                230                 235                 240 ggc agt gga tct ggg aca gat ttt act ctt acc atc agc agt gta caa      825
Gly Ser Gly Ser Gly Thr Asp Phe Thr Leu Thr Ile Ser Ser Val Gln
            245                 250                 255 gct gaa gac ctg gca gtt tat tac tgt cat caa tac ctc tcc tcg tcg      873
Ala Glu Asp Leu Ala Val Tyr Tyr Cys His Gln Tyr Leu Ser Ser Ser
260                 265                 270 acg ttc ggt gga ggg acc aag ctg gaa ata aaa cgg tcc gga ggc ggt      921
Thr Phe Gly Gly Gly Thr Lys Leu Glu Ile Lys Arg Ser Gly Gly Gly
275                 280                 285                 290 ggc tcg acc gga tgg gag acc ccc gaa ggc tgt gaa caa gtg ctc aca      969
Gly Ser Thr Gly Trp Glu Thr Pro Glu Gly Cys Glu Gln Val Leu Thr
            295                 300                 305 ggc aaa aga ctc atg cag tgt ctc cca aac cca gag gat gtg aaa atg     1017
Gly Lys Arg Leu Met Gln Cys Leu Pro Asn Pro Glu Asp Val Lys Met
        310                 315                 320 gcc ctg gag gta tat aag ctg tct ctg gaa att gaa caa ctg gaa cta     1065
Ala Leu Glu Val Tyr Lys Leu Ser Leu Glu Ile Glu Gln Leu Glu Leu
                325                 330                 335 cag aga gac agc gca aga caa tcc act ttg gat aaa gaa cta atc cac     1113
Gln Arg Asp Ser Ala Arg Gln Ser Thr Leu Asp Lys Glu Leu Ile His
            340                 345                 350 cac cat cac cat cac cat cac tga                                     1137
His His His His His His His
355                 360

<210> SEQ ID NO 4
<211> LENGTH: 361
<212> TYPE: PRT
<213> ORGANISM: artificial sequence
<220> FEATURE:
<223> OTHER INFORMATION: Synthetic Construct

<400> SEQUENCE: 4

Ala Ser Leu Glu Asn Ser Pro Val Ala Ala Met Gly Ala Gly Ala Thr
1               5                   10                  15

Gly Arg Ala Met Asp Gly Pro Arg Leu Leu Leu Leu Leu Leu Leu Gly
            20                  25                  30

Val Ser Leu Gly Gly Ala Arg Ser Gln Val Lys Leu Gln Gln Ser Gly
        35                  40                  45

Gly Gly Leu Val Gln Pro Gly Gly Ser Leu Lys Leu Ser Cys Ala Ala
    50                  55                  60

Ser Gly Phe Thr Phe Ser Ser Tyr Gly Met Ser Trp Phe Arg Gln Thr
65                  70                  75                  80

Pro Asp Lys Arg Leu Glu Leu Val Ala Ile Ile Asn Ser Asn Gly Gly
                85                  90                  95

Thr Thr Tyr Tyr Pro Asp Ser Val Lys Gly Arg Phe Thr Ile Ser Arg
            100                 105                 110

Asp Asn Ala Lys Asn Thr Leu Tyr Leu Gln Met Ser Ser Leu Lys Ser
        115                 120                 125

Glu Asp Thr Ala Met Tyr Tyr Cys Ala Arg Gly Gly Arg Trp Leu
    130                 135                 140

Leu Asp Tyr Trp Gly Gln Gly Thr Thr Val Thr Val Ser Ser Gly Gly
145                 150                 155                 160

Gly Gly Ser Gly Gly Gly Gly Ser Gly Gly Gly Gly Ser Asp Ile Glu
                165                 170                 175
```

```
Leu Thr Gln Ser Pro Ser Ser Leu Ala Val Ser Ala Gly Glu Lys Val
                180                 185                 190

Thr Met Ser Cys Lys Ser Ser Gln Ser Val Leu Tyr Ser Ser Asn Gln
            195                 200                 205

Lys Asn Tyr Leu Ala Trp Tyr Gln Gln Lys Pro Gly Gln Ser Pro Lys
        210                 215                 220

Leu Leu Ile Tyr Trp Ala Ser Thr Arg Glu Ser Gly Val Pro Asp Arg
225                 230                 235                 240

Phe Thr Gly Ser Gly Ser Gly Thr Asp Phe Thr Leu Thr Ile Ser Ser
                245                 250                 255

Val Gln Ala Glu Asp Leu Ala Val Tyr Tyr Cys His Gln Tyr Leu Ser
            260                 265                 270

Ser Ser Thr Phe Gly Gly Gly Thr Lys Leu Glu Ile Lys Arg Ser Gly
        275                 280                 285

Gly Gly Gly Ser Thr Gly Trp Glu Thr Pro Glu Gly Cys Glu Gln Val
        290                 295                 300

Leu Thr Gly Lys Arg Leu Met Gln Cys Leu Pro Asn Pro Glu Asp Val
305                 310                 315                 320

Lys Met Ala Leu Glu Val Tyr Lys Leu Ser Leu Glu Ile Glu Gln Leu
                325                 330                 335

Glu Leu Gln Arg Asp Ser Ala Arg Gln Ser Thr Leu Asp Lys Glu Leu
            340                 345                 350

Ile His His His His His His His
        355                 360

<210> SEQ ID NO 5
<211> LENGTH: 1749
<212> TYPE: DNA
<213> ORGANISM: artificial sequence
<220> FEATURE:
<223> OTHER INFORMATION: TTFgC-C4BPalpha insert for transfection in
      baculovirus
<220> FEATURE:
<221> NAME/KEY: CDS
<222> LOCATION: (1)..(1749)

<400> SEQUENCE: 5 ctg gat tgt tgg gtt gat aat gaa gaa gat ata gat gtt ata tta aaa      48
Leu Asp Cys Trp Val Asp Asn Glu Glu Asp Ile Asp Val Ile Leu Lys
1               5                   10                  15 aag agt aca att tta aat tta gat att aat aat gat att ata tca gat      96
Lys Ser Thr Ile Leu Asn Leu Asp Ile Asn Asn Asp Ile Ile Ser Asp
            20                  25                  30 ata tct ggg ttt aat tca tct gta ata aca tat cca gat gct caa ttg     144
Ile Ser Gly Phe Asn Ser Ser Val Ile Thr Tyr Pro Asp Ala Gln Leu
        35                  40                  45 gtg ccc gga ata aat ggc aaa gca ata cat tta gta aac aat gaa tct     192
Val Pro Gly Ile Asn Gly Lys Ala Ile His Leu Val Asn Asn Glu Ser
    50                  55                  60 tct gaa gtt ata gtg cat aaa gct atg gat att gaa tat aat gat atg     240
Ser Glu Val Ile Val His Lys Ala Met Asp Ile Glu Tyr Asn Asp Met
65                  70                  75                  80 ttt aat aat ttt acc gtt agc ttt tgg ttg agg gtt cct aaa gta tct     288
Phe Asn Asn Phe Thr Val Ser Phe Trp Leu Arg Val Pro Lys Val Ser
                85                  90                  95 gct agt cat tta gaa caa tat ggc aca aat gag tat tca ata att agc     336
Ala Ser His Leu Glu Gln Tyr Gly Thr Asn Glu Tyr Ser Ile Ile Ser
            100                 105                 110
```

| | | | | | | | | | | | | | | | | |
|---|---|---|---|---|---|---|---|---|---|---|---|---|---|---|---|---|
| tct | atg | aaa | aaa | cat | agt | cta | tca | ata | gga | tct | ggt | tgg | agt | gta | tca | 384 |
| Ser | Met | Lys | Lys | His | Ser | Leu | Ser | Ile | Gly | Ser | Gly | Trp | Ser | Val | Ser | |
| | | 115 | | | | 120 | | | | 125 | | | | | | |
| ctt | aaa | ggt | aat | aac | tta | ata | tgg | act | tta | aaa | gat | tcc | gcg | gga | gaa | 432 |
| Leu | Lys | Gly | Asn | Asn | Leu | Ile | Trp | Thr | Leu | Lys | Asp | Ser | Ala | Gly | Glu | |
| 130 | | | | | 135 | | | | | 140 | | | | | | |
| gtt | aga | caa | ata | act | ttt | agg | gat | tta | cct | gat | aaa | ttt | aat | gct | tat | 480 |
| Val | Arg | Gln | Ile | Thr | Phe | Arg | Asp | Leu | Pro | Asp | Lys | Phe | Asn | Ala | Tyr | |
| 145 | | | | | 150 | | | | | 155 | | | | | 160 | |
| tta | gca | aat | aaa | tgg | gtt | ttt | ata | act | att | act | aat | gat | aga | tta | tct | 528 |
| Leu | Ala | Asn | Lys | Trp | Val | Phe | Ile | Thr | Ile | Thr | Asn | Asp | Arg | Leu | Ser | |
| | | | 165 | | | | | 170 | | | | | 175 | | | |
| tct | gct | aat | ttg | tat | ata | aat | gga | gta | ctt | atg | gga | agt | gca | gaa | att | 576 |
| Ser | Ala | Asn | Leu | Tyr | Ile | Asn | Gly | Val | Leu | Met | Gly | Ser | Ala | Glu | Ile | |
| | | | 180 | | | | | 185 | | | | | 190 | | | |
| act | ggt | tta | gga | gct | att | aga | gag | gat | aat | aat | ata | aca | tta | aaa | cta | 624 |
| Thr | Gly | Leu | Gly | Ala | Ile | Arg | Glu | Asp | Asn | Asn | Ile | Thr | Leu | Lys | Leu | |
| | | 195 | | | | | 200 | | | | | 205 | | | | |
| gat | aga | tgt | aat | aat | aat | aat | caa | tac | gtt | tct | att | gat | aaa | ttt | agg | 672 |
| Asp | Arg | Cys | Asn | Asn | Asn | Asn | Gln | Tyr | Val | Ser | Ile | Asp | Lys | Phe | Arg | |
| 210 | | | | | 215 | | | | | 220 | | | | | | |
| ata | ttt | tgc | aaa | gca | tta | aat | cca | aaa | gag | att | gaa | aaa | tta | tac | aca | 720 |
| Ile | Phe | Cys | Lys | Ala | Leu | Asn | Pro | Lys | Glu | Ile | Glu | Lys | Leu | Tyr | Thr | |
| 225 | | | | | 230 | | | | | 235 | | | | | 240 | |
| agt | tat | tta | tct | ata | acc | ttt | tta | aga | gac | ttc | tgg | gga | aac | cct | tta | 768 |
| Ser | Tyr | Leu | Ser | Ile | Thr | Phe | Leu | Arg | Asp | Phe | Trp | Gly | Asn | Pro | Leu | |
| | | | | 245 | | | | | 250 | | | | | 255 | | |
| cga | tat | gat | aca | gaa | tat | tat | tta | ata | cca | gta | gct | tct | agt | tct | aaa | 816 |
| Arg | Tyr | Asp | Thr | Glu | Tyr | Tyr | Leu | Ile | Pro | Val | Ala | Ser | Ser | Ser | Lys | |
| | | | 260 | | | | | 265 | | | | | 270 | | | |
| gat | gtt | caa | ttg | aaa | aat | ata | aca | gat | tat | atg | tat | ttg | aca | aat | gcg | 864 |
| Asp | Val | Gln | Leu | Lys | Asn | Ile | Thr | Asp | Tyr | Met | Tyr | Leu | Thr | Asn | Ala | |
| | | | 275 | | | | | 280 | | | | | 285 | | | |
| cca | tcg | tat | act | aac | gga | aaa | ttg | aat | ata | tat | tat | aga | agg | tta | tat | 912 |
| Pro | Ser | Tyr | Thr | Asn | Gly | Lys | Leu | Asn | Ile | Tyr | Tyr | Arg | Arg | Leu | Tyr | |
| | | 290 | | | | | 295 | | | | | 300 | | | | |
| aat | gga | cta | aaa | ttt | att | ata | aaa | aga | tat | aca | cct | aat | aat | gaa | ata | 960 |
| Asn | Gly | Leu | Lys | Phe | Ile | Ile | Lys | Arg | Tyr | Thr | Pro | Asn | Asn | Glu | Ile | |
| 305 | | | | | 310 | | | | | 315 | | | | | 320 | |
| gat | tct | ttt | gtt | aaa | tca | ggt | gat | ttt | att | aaa | tta | tat | gta | tca | tat | 1008 |
| Asp | Ser | Phe | Val | Lys | Ser | Gly | Asp | Phe | Ile | Lys | Leu | Tyr | Val | Ser | Tyr | |
| | | | | 325 | | | | | 330 | | | | | 335 | | |
| aac | aat | aat | gag | tac | att | gta | ggt | tat | ccg | aaa | gat | gga | aat | gcc | ttt | 1056 |
| Asn | Asn | Asn | Glu | Tyr | Ile | Val | Gly | Tyr | Pro | Lys | Asp | Gly | Asn | Ala | Phe | |
| | | | 340 | | | | | 345 | | | | | 350 | | | |
| aat | aat | ctt | gat | aga | att | cta | aga | gta | ggt | tat | aat | gcc | cca | ggt | atc | 1104 |
| Asn | Asn | Leu | Asp | Arg | Ile | Leu | Arg | Val | Gly | Tyr | Asn | Ala | Pro | Gly | Ile | |
| | | 355 | | | | | 360 | | | | | 365 | | | | |
| cct | ctt | tat | aaa | aaa | atg | gaa | gca | gta | aaa | ttg | cgt | gat | tta | aaa | acc | 1152 |
| Pro | Leu | Tyr | Lys | Lys | Met | Glu | Ala | Val | Lys | Leu | Arg | Asp | Leu | Lys | Thr | |
| | | 370 | | | | | 375 | | | | | 380 | | | | |
| tat | tct | gta | caa | ctt | aaa | tta | tat | gat | gat | aaa | aat | gca | tct | tta | gga | 1200 |
| Tyr | Ser | Val | Gln | Leu | Lys | Leu | Tyr | Asp | Asp | Lys | Asn | Ala | Ser | Leu | Gly | |
| 385 | | | | | 390 | | | | | 395 | | | | | 400 | |
| cta | gta | ggt | acc | cat | aat | ggt | caa | ata | ggc | aac | gat | cca | aat | agg | gat | 1248 |
| Leu | Val | Gly | Thr | His | Asn | Gly | Gln | Ile | Gly | Asn | Asp | Pro | Asn | Arg | Asp | |
| | | | | 405 | | | | | 410 | | | | | 415 | | |
| ata | tta | att | gca | agc | aac | tgg | tac | ttt | aat | cat | tta | aaa | gat | aaa | att | 1296 |
| Ile | Leu | Ile | Ala | Ser | Asn | Trp | Tyr | Phe | Asn | His | Leu | Lys | Asp | Lys | Ile | |
| | | | 420 | | | | | 425 | | | | | 430 | | | |

```
tta gga tgt gat tgg tac ttt gta cct aca gat gaa gga tgg aca aat    1344
Leu Gly Cys Asp Trp Tyr Phe Val Pro Thr Asp Glu Gly Trp Thr Asn
            435                 440                 445 gat gcg gcc gca tcc gga ggc ggt ggc tcg gct ctg tgc cgg aaa cca    1392
Asp Ala Ala Ala Ser Gly Gly Gly Gly Ser Ala Leu Cys Arg Lys Pro
450                 455                 460 gaa tta gtg aat gga agg ttg tct gtg gat aag gat cag tat gtt gag    1440
Glu Leu Val Asn Gly Arg Leu Ser Val Asp Lys Asp Gln Tyr Val Glu
465                 470                 475                 480 cct gaa aat gtc acc atc caa tgt gat tct ggc tat ggt gtg gtt ggt    1488
Pro Glu Asn Val Thr Ile Gln Cys Asp Ser Gly Tyr Gly Val Val Gly
                485                 490                 495 ccc caa agt atc act tgc tct ggg aac aga acc tgg tac cca gag gtg    1536
Pro Gln Ser Ile Thr Cys Ser Gly Asn Arg Thr Trp Tyr Pro Glu Val
            500                 505                 510 ccc aag tgt gag tgg gag acc ccc gaa ggc tgt gaa caa gtg ctc aca    1584
Pro Lys Cys Glu Trp Glu Thr Pro Glu Gly Cys Glu Gln Val Leu Thr
            515                 520                 525 ggc aaa aga ctc atg cag tgt ctc cca aac cca gag gat gtg aaa atg    1632
Gly Lys Arg Leu Met Gln Cys Leu Pro Asn Pro Glu Asp Val Lys Met
530                 535                 540 gcc ctg gag gta tat aag ctg tct ctg gaa att gaa caa ctg gaa cta    1680
Ala Leu Glu Val Tyr Lys Leu Ser Leu Glu Ile Glu Gln Leu Glu Leu
545                 550                 555                 560 cag aga gac agc gca aga caa tcc act ttg gat aaa gaa cta atc cat    1728
Gln Arg Asp Ser Ala Arg Gln Ser Thr Leu Asp Lys Glu Leu Ile His
                565                 570                 575 cac cat cac cat cac taa taa                                        1749
His His His His His
            580

<210> SEQ ID NO 6
<211> LENGTH: 581
<212> TYPE: PRT
<213> ORGANISM: artificial sequence
<220> FEATURE:
<223> OTHER INFORMATION: Synthetic Construct

<400> SEQUENCE: 6

Leu Asp Cys Trp Val Asp Asn Glu Glu Asp Ile Asp Val Ile Leu Lys
1               5                   10                  15

Lys Ser Thr Ile Leu Asn Leu Asp Ile Asn Asn Asp Ile Ile Ser Asp
            20                  25                  30

Ile Ser Gly Phe Asn Ser Ser Val Ile Thr Tyr Pro Asp Ala Gln Leu
        35                  40                  45

Val Pro Gly Ile Asn Gly Lys Ala Ile His Leu Val Asn Asn Glu Ser
    50                  55                  60

Ser Glu Val Ile Val His Lys Ala Met Asp Ile Glu Tyr Asn Asp Met
65                  70                  75                  80

Phe Asn Asn Phe Thr Val Ser Phe Trp Leu Arg Val Pro Lys Val Ser
                85                  90                  95

Ala Ser His Leu Glu Gln Tyr Gly Thr Asn Glu Tyr Ser Ile Ile Ser
            100                 105                 110

Ser Met Lys Lys His Ser Leu Ser Ile Gly Ser Gly Trp Ser Val Ser
        115                 120                 125

Leu Lys Gly Asn Asn Leu Ile Trp Thr Leu Lys Asp Ser Ala Gly Glu
    130                 135                 140

Val Arg Gln Ile Thr Phe Arg Asp Leu Pro Asp Lys Phe Asn Ala Tyr
145                 150                 155                 160
```

```
Leu Ala Asn Lys Trp Val Phe Ile Thr Ile Thr Asn Asp Arg Leu Ser
            165                 170                 175

Ser Ala Asn Leu Tyr Ile Asn Gly Val Leu Met Gly Ser Ala Glu Ile
            180                 185                 190

Thr Gly Leu Gly Ala Ile Arg Glu Asp Asn Asn Ile Thr Leu Lys Leu
            195                 200                 205

Asp Arg Cys Asn Asn Asn Gln Tyr Val Ser Ile Asp Lys Phe Arg
210                 215                 220

Ile Phe Cys Lys Ala Leu Asn Pro Lys Glu Ile Glu Lys Leu Tyr Thr
225                 230                 235                 240

Ser Tyr Leu Ser Ile Thr Phe Leu Arg Asp Phe Trp Gly Asn Pro Leu
            245                 250                 255

Arg Tyr Asp Thr Glu Tyr Tyr Leu Ile Pro Val Ala Ser Ser Ser Lys
            260                 265                 270

Asp Val Gln Leu Lys Asn Ile Thr Asp Tyr Met Tyr Leu Thr Asn Ala
            275                 280                 285

Pro Ser Tyr Thr Asn Gly Lys Leu Asn Ile Tyr Tyr Arg Arg Leu Tyr
            290                 295                 300

Asn Gly Leu Lys Phe Ile Ile Lys Arg Tyr Thr Pro Asn Asn Glu Ile
305                 310                 315                 320

Asp Ser Phe Val Lys Ser Gly Asp Phe Ile Lys Leu Tyr Val Ser Tyr
                    325                 330                 335

Asn Asn Asn Glu Tyr Ile Val Gly Tyr Pro Lys Asp Gly Asn Ala Phe
            340                 345                 350

Asn Asn Leu Asp Arg Ile Leu Arg Val Gly Tyr Asn Ala Pro Gly Ile
            355                 360                 365

Pro Leu Tyr Lys Lys Met Glu Ala Val Lys Leu Arg Asp Leu Lys Thr
            370                 375                 380

Tyr Ser Val Gln Leu Lys Leu Tyr Asp Asp Lys Asn Ala Ser Leu Gly
385                 390                 395                 400

Leu Val Gly Thr His Asn Gly Gln Ile Gly Asn Asp Pro Asn Arg Asp
                    405                 410                 415

Ile Leu Ile Ala Ser Asn Trp Tyr Phe Asn His Leu Lys Asp Lys Ile
                    420                 425                 430

Leu Gly Cys Asp Trp Tyr Phe Val Pro Thr Asp Glu Gly Trp Thr Asn
                    435                 440                 445

Asp Ala Ala Ala Ser Gly Gly Gly Ser Ala Leu Cys Arg Lys Pro
450                 455                 460

Glu Leu Val Asn Gly Arg Leu Ser Val Asp Lys Asp Gln Tyr Val Glu
465                 470                 475                 480

Pro Glu Asn Val Thr Ile Gln Cys Asp Ser Gly Tyr Gly Val Val Gly
                    485                 490                 495

Pro Gln Ser Ile Thr Cys Ser Gly Asn Arg Thr Trp Tyr Pro Glu Val
                    500                 505                 510

Pro Lys Cys Glu Trp Glu Thr Pro Glu Gly Cys Glu Gln Val Leu Thr
                    515                 520                 525

Gly Lys Arg Leu Met Gln Cys Leu Pro Asn Pro Glu Asp Val Lys Met
            530                 535                 540

Ala Leu Glu Val Tyr Lys Leu Ser Leu Glu Ile Glu Gln Leu Glu Leu
545                 550                 555                 560
```

```
                         Gln Arg Asp Ser Ala Arg Gln Ser Thr Leu Asp Lys Glu Leu Ile His
                                         565                 570                 575

His His His His His
            580

<210> SEQ ID NO 7
<211> LENGTH: 1375
<212> TYPE: DNA
<213> ORGANISM: artificial sequence
<220> FEATURE:
<223> OTHER INFORMATION: anti-GPA-scFv-C4BPalpha insert for transfection
      in baculovirus
<220> FEATURE:
<221> NAME/KEY: CDS
<222> LOCATION: (3)..(1304)

<400> SEQUENCE: 7 aa aaa cct ata aat att ccg gat tat tca tac cgt ccc acc atc ggg         47
   Lys Pro Ile Asn Ile Pro Asp Tyr Ser Tyr Arg Pro Thr Ile Gly
   1               5                   10                  15 cgc gga tct atg cta cta gta aat cag tca cac caa ggc ttc aat aag        95
Arg Gly Ser Met Leu Leu Val Asn Gln Ser His Gln Gly Phe Asn Lys
                20                  25                  30 gaa cac aca agc aag atg gta agc gct att gtt tta tat gtg ctt ttg       143
Glu His Thr Ser Lys Met Val Ser Ala Ile Val Leu Tyr Val Leu Leu
            35                  40                  45 gcg gcg gcg gcg cat tct gcc ttt gcg gcg gat cta tgg atc ccg ggg       191
Ala Ala Ala Ala His Ser Ala Phe Ala Ala Asp Leu Trp Ile Pro Gly
        50                  55                  60 cag gtg aaa ctg cag cag tca ggg gga ggc tta gtg cag cct gga ggg       239
Gln Val Lys Leu Gln Gln Ser Gly Gly Gly Leu Val Gln Pro Gly Gly
    65                  70                  75 tcc ctg aaa ctc tcc tgt gca gcc tct gga ttc act ttc agt agc tat       287
Ser Leu Lys Leu Ser Cys Ala Ala Ser Gly Phe Thr Phe Ser Ser Tyr
80                  85                  90                  95 ggc atg tct tgg ttt cgc cag act cca gac aag agg ctg gag ttg gtc       335
Gly Met Ser Trp Phe Arg Gln Thr Pro Asp Lys Arg Leu Glu Leu Val
                100                 105                 110 gca atc att aat agt aat ggt ggt act acc tat tat cca gac agt gtg       383
Ala Ile Ile Asn Ser Asn Gly Gly Thr Thr Tyr Tyr Pro Asp Ser Val
            115                 120                 125 aag ggc cga ttc acc atc tcc aga gac aat gcc aag aac acc ctg tac       431
Lys Gly Arg Phe Thr Ile Ser Arg Asp Asn Ala Lys Asn Thr Leu Tyr
        130                 135                 140 ctg caa atg agc agt ctg aag tct gag gac aca gcc atg tat tac tgt       479
Leu Gln Met Ser Ser Leu Lys Ser Glu Asp Thr Ala Met Tyr Tyr Cys
    145                 150                 155 gca aga gga gga ggg aga tgg tta ctg gac tac tgg ggc caa ggg acc       527
Ala Arg Gly Gly Gly Arg Trp Leu Leu Asp Tyr Trp Gly Gln Gly Thr
160                 165                 170                 175 acg gtc acc gtc tcc tca ggt gga ggc ggg tca ggc gga ggt ggc tct       575
Thr Val Thr Val Ser Ser Gly Gly Gly Gly Ser Gly Gly Gly Gly Ser
                180                 185                 190 ggc ggt ggc gga tcg gac atc gag ctc act cag tct cca tca tct ctg       623
Gly Gly Gly Gly Ser Asp Ile Glu Leu Thr Gln Ser Pro Ser Ser Leu
            195                 200                 205 gct gtg tct gca gga gaa aag gtc act atg agc tgt aag tcc agt caa       671
Ala Val Ser Ala Gly Glu Lys Val Thr Met Ser Cys Lys Ser Ser Gln
        210                 215                 220 agt gtt tta tac agt tca aat cag aag aac tac ttg gcc tgg tac cag       719
Ser Val Leu Tyr Ser Ser Asn Gln Lys Asn Tyr Leu Ala Trp Tyr Gln
    225                 230                 235
```

```
cag aaa cca ggg cag tct cct aaa ctg ctg atc tac tgg gca tcc act      767
Gln Lys Pro Gly Gln Ser Pro Lys Leu Leu Ile Tyr Trp Ala Ser Thr
240                 245                 250                 255 agg gaa tct ggt gtc cct gat cgc ttc aca ggc agt gga tct ggg aca      815
Arg Glu Ser Gly Val Pro Asp Arg Phe Thr Gly Ser Gly Ser Gly Thr
                260                 265                 270 gat ttt act ctt acc atc agc agt gta caa gct gaa gac ctg gca gtt      863
Asp Phe Thr Leu Thr Ile Ser Ser Val Gln Ala Glu Asp Leu Ala Val
            275                 280                 285 tat tac tgt cat caa tac ctc tcc tcg tcg acg ttc ggt gga ggg acc      911
Tyr Tyr Cys His Gln Tyr Leu Ser Ser Ser Thr Phe Gly Gly Gly Thr
        290                 295                 300 aag ctg gaa ata aaa cgg gcg gcc gca tcc gga ggc ggt ggc tcg gct      959
Lys Leu Glu Ile Lys Arg Ala Ala Ala Ser Gly Gly Gly Gly Ser Ala
    305                 310                 315 ctg tgc cgg aaa cca gaa tta gtg aat gga agg ttg tct gtg gat aag     1007
Leu Cys Arg Lys Pro Glu Leu Val Asn Gly Arg Leu Ser Val Asp Lys
320                 325                 330                 335 gat cag tat gtt gag cct gaa aat gtc acc atc caa tgt gat tct ggc     1055
Asp Gln Tyr Val Glu Pro Glu Asn Val Thr Ile Gln Cys Asp Ser Gly
                340                 345                 350 tat ggt gtg gtt ggt ccc caa agt atc act tgc tct ggg aac aga acc     1103
Tyr Gly Val Val Gly Pro Gln Ser Ile Thr Cys Ser Gly Asn Arg Thr
            355                 360                 365 tgg tac cca gag gtg ccc aag tgt gag tgg gag acc ccc gaa ggc tgt     1151
Trp Tyr Pro Glu Val Pro Lys Cys Glu Trp Glu Thr Pro Glu Gly Cys
        370                 375                 380 gaa caa gtg ctc aca ggc aaa aga ctc atg cag tgt ctc cca aac cca     1199
Glu Gln Val Leu Thr Gly Lys Arg Leu Met Gln Cys Leu Pro Asn Pro
    385                 390                 395 gag gat gtg aaa atg gcc ctg gag gta tat aag ctg tct ctg gaa att     1247
Glu Asp Val Lys Met Ala Leu Glu Val Tyr Lys Leu Ser Leu Glu Ile
400                 405                 410                 415 gaa caa ctg gaa cta cag aga gac agc gca aga caa tcc act ttg gat     1295
Glu Gln Leu Glu Leu Gln Arg Asp Ser Ala Arg Gln Ser Thr Leu Asp
                420                 425                 430 aaa gaa cta taataagatc tgatcctttc ctgggacccg gcaagaacca             1344
Lys Glu Leu aaaactcact ctcttcaagg aaatccgtaa t                                  1375

<210> SEQ ID NO 8
<211> LENGTH: 434
<212> TYPE: PRT
<213> ORGANISM: artificial sequence
<220> FEATURE:
<223> OTHER INFORMATION: Synthetic Construct

<400> SEQUENCE: 8

Lys Pro Ile Asn Ile Pro Asp Tyr Ser Tyr Arg Pro Thr Ile Gly Arg
1               5                   10                  15

Gly Ser Met Leu Leu Val Asn Gln Ser His Gln Gly Phe Asn Lys Glu
            20                  25                  30

His Thr Ser Lys Met Val Ser Ala Ile Val Leu Tyr Val Leu Leu Ala
        35                  40                  45

Ala Ala Ala His Ser Ala Phe Ala Ala Asp Leu Trp Ile Pro Gly Gln
    50                  55                  60

Val Lys Leu Gln Gln Ser Gly Gly Gly Leu Val Gln Pro Gly Gly Ser
65                  70                  75                  80
```

Leu Lys Leu Ser Cys Ala Ala Ser Gly Phe Thr Ser Ser Tyr Gly
            85                  90                  95

Met Ser Trp Phe Arg Gln Thr Pro Asp Lys Arg Leu Glu Leu Val Ala
        100                 105                 110

Ile Ile Asn Ser Asn Gly Gly Thr Thr Tyr Tyr Pro Asp Ser Val Lys
        115                 120                 125

Gly Arg Phe Thr Ile Ser Arg Asp Asn Ala Lys Asn Thr Leu Tyr Leu
130                 135                 140

Gln Met Ser Ser Leu Lys Ser Glu Asp Thr Ala Met Tyr Tyr Cys Ala
145                 150                 155                 160

Arg Gly Gly Gly Arg Trp Leu Leu Asp Tyr Trp Gly Gln Gly Thr Thr
                165                 170                 175

Val Thr Val Ser Ser Gly Gly Gly Gly Ser Gly Gly Gly Gly Ser Gly
            180                 185                 190

Gly Gly Gly Ser Asp Ile Glu Leu Thr Gln Ser Pro Ser Ser Leu Ala
        195                 200                 205

Val Ser Ala Gly Glu Lys Val Thr Met Ser Cys Lys Ser Ser Gln Ser
    210                 215                 220

Val Leu Tyr Ser Ser Asn Gln Lys Asn Tyr Leu Ala Trp Tyr Gln Gln
225                 230                 235                 240

Lys Pro Gly Gln Ser Pro Lys Leu Leu Ile Tyr Trp Ala Ser Thr Arg
                245                 250                 255

Glu Ser Gly Val Pro Asp Arg Phe Thr Gly Ser Gly Ser Gly Thr Asp
            260                 265                 270

Phe Thr Leu Thr Ile Ser Ser Val Gln Ala Glu Asp Leu Ala Val Tyr
        275                 280                 285

Tyr Cys His Gln Tyr Leu Ser Ser Ser Thr Phe Gly Gly Gly Thr Lys
    290                 295                 300

Leu Glu Ile Lys Arg Ala Ala Ala Ser Gly Gly Gly Gly Ser Ala Leu
305                 310                 315                 320

Cys Arg Lys Pro Glu Leu Val Asn Gly Arg Leu Ser Val Asp Lys Asp
                325                 330                 335

Gln Tyr Val Glu Pro Glu Asn Val Thr Ile Gln Cys Asp Ser Gly Tyr
            340                 345                 350

Gly Val Val Gly Pro Gln Ser Ile Thr Cys Ser Gly Asn Arg Thr Trp
        355                 360                 365

Tyr Pro Glu Val Pro Lys Cys Glu Trp Glu Thr Pro Glu Gly Cys Glu
370                 375                 380

Gln Val Leu Thr Gly Lys Arg Leu Met Gln Cys Leu Pro Asn Pro Glu
385                 390                 395                 400

Asp Val Lys Met Ala Leu Glu Val Tyr Lys Leu Ser Leu Glu Ile Glu
                405                 410                 415

Gln Leu Glu Leu Gln Arg Asp Ser Ala Arg Gln Ser Thr Leu Asp Lys
            420                 425                 430

Glu Leu

<210> SEQ ID NO 9
<211> LENGTH: 33
<212> TYPE: DNA
<213> ORGANISM: artificial sequence
<220> FEATURE:
<223> OTHER INFORMATION: primer

<400> SEQUENCE: 9
cgcgagagat ctctggattg ttgggttgat aat                              33

```
<210> SEQ ID NO 10
<211> LENGTH: 33
<212> TYPE: DNA
<213> ORGANISM: artificial sequence
<220> FEATURE:
<223> OTHER INFORMATION: primer

<400> SEQUENCE: 10
cgcgagtccg gaatcatttg tccatccttc atc                           33

<210> SEQ ID NO 11
<211> LENGTH: 30
<212> TYPE: DNA
<213> ORGANISM: artificial sequence
<220> FEATURE:
<223> OTHER INFORMATION: primer

<400> SEQUENCE: 11
cgcgagtccg gaggcggtgg ctcgaccgga                               30

<210> SEQ ID NO 12
<211> LENGTH: 57
<212> TYPE: DNA
<213> ORGANISM: artificial sequence
<220> FEATURE:
<223> OTHER INFORMATION: primer

<400> SEQUENCE: 12
cgcgagtcta gattatcagt gatggtgatg gtgatggtgg tggattagtt ctttatc    57

<210> SEQ ID NO 13
<211> LENGTH: 30
<212> TYPE: DNA
<213> ORGANISM: artificial sequence
<220> FEATURE:
<223> OTHER INFORMATION: primer

<400> SEQUENCE: 13
cgcgagagat ctcaggtgaa actgcagcag                               30

<210> SEQ ID NO 14
<211> LENGTH: 30
<212> TYPE: DNA
<213> ORGANISM: artificial sequence
<220> FEATURE:
<223> OTHER INFORMATION: primer

<400> SEQUENCE: 14
cgcgagtccg gaccgtttta tttccagctt                               30

<210> SEQ ID NO 15
<211> LENGTH: 33
<212> TYPE: DNA
<213> ORGANISM: artificial sequence
<220> FEATURE:
<223> OTHER INFORMATION: primer

<400> SEQUENCE: 15
cgcgaggcgg ccgcccgttt tatttccagc ttg                           33

<210> SEQ ID NO 16
<211> LENGTH: 33
<212> TYPE: DNA
<213> ORGANISM: artificial sequence
<220> FEATURE:
<223> OTHER INFORMATION: primer
```

<400> SEQUENCE: 16
cgcgaggcgg ccgcatccgg aggcggtggc tcg               33

<210> SEQ ID NO 17
<211> LENGTH: 52
<212> TYPE: DNA
<213> ORGANISM: artificial sequence
<220> FEATURE:
<223> OTHER INFORMATION: primer

<400> SEQUENCE: 17
cgagtctaga tcagtgatgg tgatggtgat ggatcaacaa ttttgccttc aa      52

<210> SEQ ID NO 18
<211> LENGTH: 30
<212> TYPE: DNA
<213> ORGANISM: artificial sequence
<220> FEATURE:
<223> OTHER INFORMATION: primer

<400> SEQUENCE: 18
cgcgagagat ctgaggtgca gctggtggag               30

<210> SEQ ID NO 19
<211> LENGTH: 30
<212> TYPE: DNA
<213> ORGANISM: artificial sequence
<220> FEATURE:
<223> OTHER INFORMATION: primer

<400> SEQUENCE: 19
cgcgagtccg gatgaggaga cagtgacctg               30

<210> SEQ ID NO 20
<211> LENGTH: 34
<212> TYPE: DNA
<213> ORGANISM: artificial sequence
<220> FEATURE:
<223> OTHER INFORMATION: primer

<400> SEQUENCE: 20
cgcgagcccg gggcaggtga aactgcagca gtct               34

<210> SEQ ID NO 21
<211> LENGTH: 34
<212> TYPE: DNA
<213> ORGANISM: artificial sequence
<220> FEATURE:
<223> OTHER INFORMATION: primer

<400> SEQUENCE: 21
cgcgaggcgg ccgcccgttt tatttcagct tggt               34

<210> SEQ ID NO 22
<211> LENGTH: 33
<212> TYPE: DNA
<213> ORGANISM: artificial sequence
<220> FEATURE:
<223> OTHER INFORMATION: primer

<400> SEQUENCE: 22
cgcgaggcgg ccgcatccgg aggcggtggc tcg               33

-continued

```
<210> SEQ ID NO 23
<211> LENGTH: 33
<212> TYPE: DNA
<213> ORGANISM: artificial sequence
<220> FEATURE:
<223> OTHER INFORMATION: primer

<400> SEQUENCE: 23
cgcgagagat cttattacaa caattttgcc ttc                              33

<210> SEQ ID NO 24
<211> LENGTH: 35
<212> TYPE: DNA
<213> ORGANISM: artificial sequence
<220> FEATURE:
<223> OTHER INFORMATION: primer

<400> SEQUENCE: 24
cgcgagcccg gggctggatt gttgggttga taatg                            35
```